United States Patent
Liszka et al.

(10) Patent No.: US 11,118,204 B2
(45) Date of Patent: *Sep. 14, 2021

(54) SWITCHABLE IONIC LIQUIDS FOR BIOMASS PRETREATMENT AND ENZYMATIC HYDROLYSIS

(71) Applicant: National Technology & Engineering Solutions of Sandia, LLC, Albuquerque, NM (US)

(72) Inventors: Michael Liszka, Berkeley, CA (US); Kenneth Sale, Livermore, CA (US); Blake Simmons, San Francisco, CA (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 147 days.

This patent is subject to a terminal disclaimer.

(21) Appl. No.: 15/523,355

(22) PCT Filed: Oct. 30, 2015

(86) PCT No.: PCT/US2015/058472
§ 371 (c)(1),
(2) Date: Apr. 28, 2017

(87) PCT Pub. No.: WO2016/070125
PCT Pub. Date: May 6, 2016

(65) Prior Publication Data
US 2017/0247729 A1 Aug. 31, 2017

Related U.S. Application Data

(60) Provisional application No. 62/073,802, filed on Oct. 31, 2014.

(51) Int. Cl.
| | | |
|---|---|---|
| *C12P 19/14* | (2006.01) | |
| *C12P 7/04* | (2006.01) | |
| *C13K 1/02* | (2006.01) | |
| *C08H 8/00* | (2010.01) | |
| *C13K 13/00* | (2006.01) | |
| *C12P 5/00* | (2006.01) | |
| *C12P 19/02* | (2006.01) | |

(52) U.S. Cl.
CPC .......... *C12P 19/14* (2013.01); *C08H 8/00* (2013.01); *C12P 5/002* (2013.01); *C12P 5/007* (2013.01); *C12P 7/04* (2013.01); *C12P 19/02* (2013.01); *C13K 1/02* (2013.01); *C13K 13/002* (2013.01); *C12P 2201/00* (2013.01)

(58) Field of Classification Search
CPC ................................................ C12P 2201/00
See application file for complete search history.

(56) References Cited

U.S. PATENT DOCUMENTS

| 4,865,973 A | 9/1989 | Kollerup et al. | |
|---|---|---|---|
| 8,187,489 B1 | 5/2012 | Davis et al. | |
| 2010/0285552 A1* | 11/2010 | Varanasi .................. | C12N 1/18 435/161 |
| 2012/0301948 A1 | 11/2012 | Brennan et al. | |
| 2014/0004563 A1* | 1/2014 | Paripati .................. | C07K 1/145 435/68.1 |
| 2014/0220651 A1 | 8/2014 | Raines et al. | |

OTHER PUBLICATIONS

Ohno et al., Amino Acid Ionic Liquids, Acc. Chem. Res. 2007, 40, 1122-1129.*
Hou et al., Evaluation of Toxicity and Biodegradability of Cholinium Amino Acids Ionic Liquids, PLOS ONE Mar. 2013, vol. 8, Issue 3 e59145.*
Zdanowicz et al., Polimery, 2011,56:861-864.*
Boissou et al., "Transition of cellulose crystalline structure in biodegradable mixtures of renewably-sourced levulinate alkyl ammonium ionic liquids, γ-valerolactone and water," Green Chem., 2014, 16, 2463-2471.
Huang et al., "A review of separation technologies in current and future biorefineries," Separation and Purification Technology, 2008, 62, 1-21.
Liu et al., "MEP pathway-mediated isopentenol production in metabolically engineered *Escherichia coli*", Microbial Cell Factories, vol. 13, Article 135, Sep. 12, 2014, 7 pages.
Liu et al., "Ionic liquids from renewable biomaterials: synthesis, characterization and application in the pretreatement of biomass," Green Chem, 2012, 14, 304-307.
PCT/US2015/058472 , "International Search Report and Written Opinion", dated Feb. 11, 2016, 4 pages.
Shi et al., "One-pot ionic liquid pretreatment and saccharification of switchgrass," Green Chem., 2013, 15, 2579-2589.
Sun et al., "Understanding pretreatment efficacy of four cholinium and imidazolium ionic liquids by chemistry and computation," Green Chem., 2014, 16, 2546-2557.

* cited by examiner

*Primary Examiner* — Bin Shen
(74) *Attorney, Agent, or Firm* — Kilpatrick Townsend & Stockton LLP

(57) ABSTRACT

In one aspect, the present invention provides a method for preparing a sugar composition. The method includes: forming a mixture including polysaccharide biomass and an ionic liquid solution, wherein the ionic liquid solution contains water and an ionic liquid, and wherein the ionic liquid contains a dicarboxylic acid anion and a cation. The pH of the mixture is greater than or equal to about 10, and the molar ratio of the dicarboxylic acid anion to the cation is at least about 1:2. The method further includes: maintaining the mixture under conditions sufficient to dissolve at least a portion of the polysaccharide present in the polysaccharide biomass; reducing the pH of the mixture containing the dissolved polysaccharide to at least about 7; adding at least one glycoside hydrolase to the mixture having the reduced pH.

17 Claims, 9 Drawing Sheets

SWITCHABLE IONIC LIQUIDS FOR BIOMASS PRETREATMENT AND ENZYMATIC HYDROLYSIS

CROSS REFERENCES TO RELATED APPLICATIONS

The present application is a U.S. National Stage Entry of International Pat. Appl. No. PCT/US2015/058472, filed Oct. 30, 2015, which claims priority to U.S. Provisional Pat. Appl. No. 62/073,802, filed on Oct. 31, 2014, which applications are incorporated herein by reference in their entirety.

STATEMENT AS TO RIGHTS TO INVENTIONS MADE UNDER FEDERALLY SPONSORED RESEARCH AND DEVELOPMENT

The invention described and claimed herein was made utilizing funds supplied by the U.S. Department of Energy under Contract No. DE-AC02-05CH11231. The government has certain rights in this invention.

BACKGROUND OF THE INVENTION

In recent years, tremendous efforts have been made to develop biofuels made from lignocellulosic biomass, which is derived from agricultural wastes, forest residues, and dedicated energy crops. However, one of the greatest limitations facing the economic viability of this technology is the recalcitrant nature of the lignocellulosic biomass to enzymatic hydrolysis into its component sugars. This resistance to breakdown necessitates the use of pretreatment steps to enhance the accessibility to and hydrolysis of the carbohydrate components present in the lignocellulosic biomass. Most pretreatment processes are thermo-chemical processes that utilize combinations of high temperatures and pressures, or dilute acids or alkalis, to open up the structure of the biomass. Such processes necessitate the use of specialized equipment and high-energy inputs.

Ionic liquids (ILs) have come into prominence over recent years and have been used as innovative fluids for chemical processing. They are known as environmentally friendly solvents primarily due to their low volatility and their potential recyclability. Recently, the use of ILs for the pretreatment of biomass has been shown to be a promising technology, allowing for the solubilization of crystalline cellulose and biomass under relatively mild conditions. Reconstitution of the biomass from the IL results in an amorphous product that significantly increases the rate of enzymatic hydrolysis to its component soluble sugars. For instance, the IL 1-ethyl-3-methylimidazolium acetate $[C_2Mim][OAc]$ has been found to be effective at the dissolution of biomass and the subsequent enhancement of enzymatic hydrolysis (also termed saccharification).

The ionic liquid pretreatment process can generally be described as the dissolution of biomass into the ionic liquid at an elevated temperature with stirring, followed by the optional addition of a precipitant (or, alternatively, an anti-solvent) that precipitates the biomass from solution. This precipitant or anti-solvent is typically either water or ethanol, or some other solvent with hydrogen bonding capacity. Once the biomass has been precipitated, solid/liquid separation and downstream enzymatic hydrolysis of the now amorphous biomass results in monosaccharides suitable for fermentation. Typically, the ionic liquid pretreatment process employs atmospheric pressure and temperatures ranging from about 120° C. to 160° C. Recycling of ionic liquid can be achieved by distillation of the precipitating solvent.

Although pretreatment with ionic liquids has met with success, ionic liquids are expensive and the pretreatment process is both energy and time intensive. Furthermore, ionic liquids can destabilize cellulases used for hydrolysis and inhibit the growth of microorganisms used for subsequent fermentation of the component soluble sugars. As such, what is needed are methods for processing biomass in which pretreatment, hydrolysis, and fermentation steps are compatible with each other. Use of ionic liquids that are renewably sourced and non-toxic are particularly desired. The present invention provides methods that fulfill these and other needs.

BRIEF SUMMARY OF EMBODIMENTS OF THE INVENTION

In one aspect, the present invention provides a method for preparing a sugar composition. In one aspect, the method comprises:
i) forming a mixture including polysaccharide biomass and an ionic liquid solution, wherein
the ionic liquid solution contains water and an ionic liquid,
the ionic liquid contains a dicarboxylic acid anion and a cation,
the pH of the mixture is greater than or equal to about 10, and
the molar ratio of the dicarboxylic acid anion to the cation is at least about 1:2;
ii) maintaining the mixture under conditions sufficient to dissolve at least a portion of the polysaccharide present in the polysaccharide biomass;
iii) reducing the pH of the mixture containing the dissolved polysaccharide to at least about 7;
iv) adding at least one glycoside hydrolase to the mixture having the reduced pH; and
v) maintaining the mixture containing the glycoside hydrolase under conditions sufficient to hydrolyze at least a portion of the dissolved polysaccharide, thereby forming the sugar composition;
wherein the sugar composition contains at least one monosaccharide or oligosaccharide, or a combination thereof.

In some embodiments, the polysaccharide biomass comprises lignocellulose.

In some embodiments, the dicarboxylic acid is selected from succinic acid and glutamic acid. In some embodiments, the cation is choline. In some embodiments, the ionic liquid solution contains:
75-90% (w/w) water; and
10-25% dicholine glutamate (w/w); or
10-25% dicholine succinate (w/w).

In some embodiments, step iii) includes adding the same dicarboxylic acid used in step i) to the mixture resulting from step ii).

In some embodiments, the glycoside hydrolase is a cellulase. In some embodiments, the glycoside hydrolase is selected from an endoglucanase, an exoglucanase, a β-glucosidase, a xylanase, and mixtures thereof.

In some embodiments, the method further includes:
i) fermenting the sugar composition.

Further aspects and embodiments of the invention are described in detail below.

DETAILED DESCRIPTION OF THE INVENTION

I. General

Figure 1A:
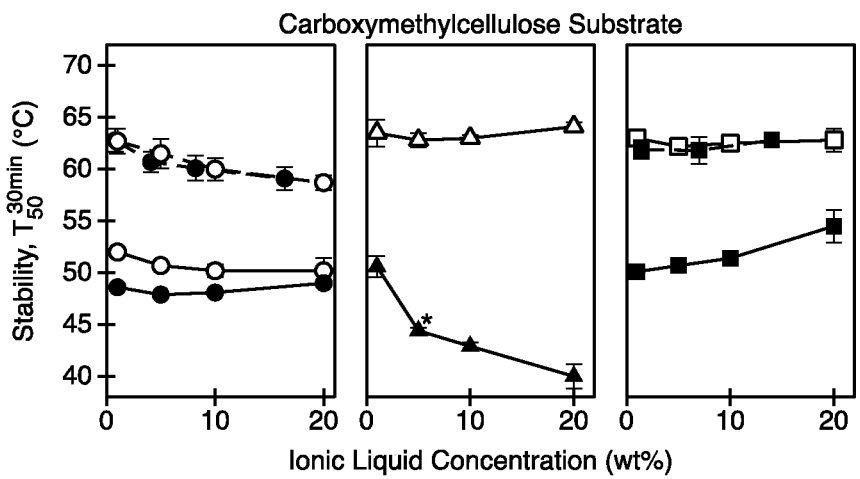
FIG. 1A shows the stability of Ctec2 in ionic liquids as a function of concentration, assessed using carboxymethylcellulose as the enzyme substrate.

The present invention is based, in part, on the discovery that dicarboxylic acid-based ionic liquids can be manipulated to provide high biomass pretreatment efficiency, stabilization of commercial enzyme mixtures, and compatibility with microbial fermentation. The system takes advantage of the two ionization states of dicarboxylic acids to switch from a basic solution that pretreats biomass effectively to an acidic solution with conditions favorable for enzymes that break down polysaccharide biomass, including cellulases and other glycoside hydrolases. High conversion of biomass to fermentable sugars can be achieved. These sugars can be converted to products such as ethanol, isopentenol and bisabolines by fermentation of crude hydrolysates with various organisms, such as *E. coli* or a yeast, e.g., *Saccharomyces cerevisiae*, or other known microorganisms or fungi for fermentation. The methods of the invention can be used to overcome limitations associated with known ionic liquid processes.

II. Definitions

As used herein, the term "sugar composition" refers to a mixture containing one or more monosaccharides, oligosaccharides, or combinations thereof. Sugar compositions prepared according to the methods of the invention are also referred to as "hydrolysates" in the present application.

As used herein, the term "monosaccharide" refers to a sugar having a five-membered carbon backbone (i.e., a pentose) or a six-membered carbon backbone (i.e., a hexose). Examples of monosaccharides include, but are not limited to, glucose, ribose, fucose, xylose, arabinose, galactose, mannose, glucuronic acid, and iduronic acid. Monosaccharides also include pentoses and hexoses substituted with hydroxy groups, oxo groups, amino groups, acetylamino groups, and other functional groups.

As used herein, the term "oligosaccharide" refers to a compound containing at least two sugars covalently linked together. Oligosaccharides include disaccharides, trisaccharides, tetrasaccharides, pentasaccharides, hexasaccharides, heptasaccharides, octasaccharides, and the like. Covalent linkages for linking sugars generally consist of glycosidic linkages (i.e., C—O—C bonds) formed from the hydroxyl groups of adjacent sugars. Linkages can occur between the 1-carbon (the anomeric carbon) and the 4-carbon of adjacent sugars (i.e., a 1-4 linkage), the 1-carbon (the anomeric carbon) and the 3-carbon of adjacent sugars (i.e., a 1-3 linkage), the 1-carbon (the anomeric carbon) and the 6-carbon of adjacent sugars (i.e., a 1-6 linkage), or the 1-carbon (the anomeric carbon) and the 2-carbon of adjacent sugars (i.e., a 1-2 linkage). Other linkages can be present in the oligosaccharide, depending on the particular sugar subunits present. Those of skill in the art will appreciate that a sugar can be linked within an oligosaccharide such that the glycosidic bond at the anomeric carbon is in the α- or β-configuration.

As used herein, the term "polysaccharide" generally refers to a compound containing 10 or more sugars linked together as described for oligosaccharides.

As used herein, the term "biomass" and "polysaccharide biomass" are used interchangeably to refer to plant-based material that includes a plurality of components such as lignin, cellulose, and hemicellulose. Sources of biomass includes trees, shrubs, grasses, wheat, wheat straw, sugar cane bagasse, corn, corn husks, corn kernel including fiber from kernels, products and by-products from milling of grains such as corn, rice, wheat, and barley, as well as municipal solid waste, waste paper, and yard waste. Biomass sources can also include herbaceous material, agricultural residues, forestry residues, and paper mill residues. Additional examples include branches, bushes, canes, corn and corn husks, energy crops, forests, fruits, flowers, grains, grasses, herbaceous crops, leaves, bark, needles, logs, roots, saplings, short rotation woody crops, shrubs, switchgrasses, trees, vegetables, fruit peels, vines, sugar beet pulp, wheat midlings, oat hulls, hard and soft woods, organic waste materials generated from agricultural processes including farming and forestry activities, or mixtures thereof.

As used herein, the term "lignocellulosic biomass" refers to natural and/or synthetic materials containing lignin, cellulose, and/or hemicellulose. Generally, these materials also contain (but need not contain) xylan, protein, and/or other carbohydrates, such as starch.

As used herein, the term "cellulose" refers to refers to a homopolymer of β(1→4) linked D-glucose units that form a linear chain. Cellulose can contain several hundred to several thousand or more glucose units, making cellulose a polysaccharide.

As used herein, the term "hemicellulose" refers to a heteropolymer containing different saccharide units, including but not limited to, xylose, mannose, galactose, rhamnose and arabinose. Hemicellulose forms a branched polymer with several hundred to several thousand sugar units. Hemicellulose can include both pentose and hexose sugars.

As use herein, the term "lignin" refers to a phenylpropane polymer of monolignol monomers (p-coumaryl alcohol, coniferyl alcohol, and sinapyl alcohol) found as an integral part of the secondary cell walls of plants and certain types of algae As used herein, the term "ionic liquid" refers to an organic salt that is a liquid at room temperature rather than a solid or crystalline substance. Ionic liquids typically exhibit a number of advantageous properties, including low volatility, thermal stability, and the ability to dissolve a wide range of solutes under mild conditions.

As used herein, the term "alkyl" refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can also refer to alkyl groups having up to 20 carbons atoms, such as, but not limited to heptyl, octyl, nonyl, decyl, etc. An "alkane" refers to the parent compound of the alkyl radicals described herein.

As used herein, the term "alkenyl" refers to a straight chain or branched hydrocarbon having at least 2 carbon atoms and at least one double bond. Alkenyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Alkenyl groups can have any suitable number of double bonds, including, but not limited to, 1, 2, 3, 4, 5 or more. Examples of alkenyl groups include, but are not limited to, vinyl (ethenyl), propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl. An "alkene" refers to the parent compound of the alkenyl radicals described herein.

As used herein, the term "dicarboxylic acid" refers to and alkane or alkene having two carboxy moieties (i.e., —COOH groups). As used herein, the term "dicarboxylic acid anion" refers to a dicarboxylic acid wherein one or two of the carboxy moieties is deprotonated (i.e., present as a —COO⁻ anion). Dicarboxylic acid anions are generally bound to cations in an ionic liquid via electrostatic interaction.

As used herein, the term "cation" refers to a positively charged molecule that pairs with an anion in an ionic liquid via electrostatic interaction. Examples of cations suitable for inclusion in ionic liquids include, but are not limited to, ammonium, imidazolium, pyridinium, sulfonium, and phosphonium cations.

As used herein, the term "molar ratio" refers to the number of moles of one species in a mixture relative to the number of moles of a second species in the mixture. As a non-limiting example, an ionic liquid having an anion:cation ratio of 1:2 has at least two moles of the cation for every mole of the anion. For ionic liquids where the molar ratio of the anion to the cation is at least 1:2, the molar ratio can be, e.g., 1:2.1, 1:2.5, or 1:3, or 1:4.

As used herein, the term "choline" refers to the 2-hydroxy-N,N,N-trimethylethanamonium cation and salts thereof (e.g., 2-hydroxy-N,N,N-trimethylethanamonium hydroxide). The term "dicholine glutamate," also referred to as [Ch]₂[Glu], refers to an ionic liquid having glutamic acid dianions and two choline cations for each of the glutamic acid dianions. As used herein, the term "dicholine succinate," also referred to as [Ch]₂[Su], refers to an ionic liquid having succinic acid dianions and two choline cations for each of the succinic acid dianions.

As used herein, the term "pH" refers to refers to a measurement of the concentration of hydrogen ions in a mixture such as an aqueous solution. pH is expressed as the decimal logarithm (i.e., $\log_{10}$) of the reciprocal of the hydrogen ion concentration in the mixture. The pH of a mixture can be determined using a number of known techniques. One of skill in the art will know how to adjust the pH of a mixture by adding acids and/or bases to the mixture.

As used herein, the term "acid" refers to a substance that is capable of donating a proton (i.e., a hydrogen cation) to form a conjugate base of the acid. Examples of acids include, but are not limited to, hydrochloric acid, sulfuric acid, acetic acid, and formic acid.

As used herein, the term "base" refers to a substance that is capable of accepting a proton (i.e., a hydrogen cation) to form a conjugate acid of the base. Examples of bases include, but are not limited to, sodium hydroxide, potassium hydroxide, sodium bicarbonate, and potassium carbonate.

As used herein, the terms "dissolve" and "dissolution" refer to the solvation of a solute with a solvent to form a solution. More particularly, dissolution refers to the partial or complete solubilization of biomass in an ionic liquid or an ionic liquid solution. In the methods of the invention, dissolution of lignocellulosic biomass can include partial or complete disruption of intra- and intermolecular hydrogen bonds present in cellulose polymer chains, partial or complete disruption of interactions between cellulose and hemicellulose, and partial or complete solubilization of lignin.

The terms "hydrolyze," "hydrolysis," and "saccharification," when used herein with respect to polysaccharide chemistry, refer to the cleavage of one or more glycosidic bonds in an oligosaccharide or a polysaccharide by water. The hydrolysis is typically catalyzed by an enzyme such as a glycoside hydrolase. Hydrolysis can also be promoted by addition of a catalyst such as an acid or base.

As used herein, the term "glycoside hydrolase" refers to an enzyme that catalyzes the cleavage of the glycosidic linkage in oligosaccharides or polysaccharides by water to release smaller sugars.

As used herein, the terms "fermenting" and "fermentation" refer to a metabolic process performed by an organism that converts one substrate to another, such as when an organism utilizes glucose and converts it to ethanol or propionic acid. In the present invention "fermentation" is typically used broadly to refer to the conversion of simple sugars to a desired product.

The terms "about" and "around," as used herein to modify a numerical value, indicate a close range surrounding that explicit value. If "X" were the value, "about X" or "around X" would indicate a value from 0.9X to 1.1X. "About X" thus includes, for example, a value from 0.95X to 1.05X. Any reference to "about X" or "around X" specifically indicates at least the values X, 0.90X, 0.91X, 0.92X, 0.93X, 0.94X, 0.95X, 0.96X, 0.97X, 0.98X, 0.99X, 1.01X, 1.02X, 1.03X, 1.04X, 1.05X, 1.07X, 1.08X, 1.09X, and 1.10X. Accordingly, "about X" and "around X" are intended to teach and provide written description support for a claim limitation of, e.g., "0.98X."

III. Embodiments of the Invention

In one aspect, the present invention provides a method for preparing a sugar composition. In typical embodiments, a method of the invention, includes:
i) forming a mixture including polysaccharide biomass and an ionic liquid solution, wherein
the ionic liquid solution contains water and an ionic liquid,
the ionic liquid contains a dicarboxylic acid anion and a cation,
the pH of the mixture is greater than or equal to about 10, and
the molar ratio of the dicarboxylic acid anion to the cation is at least about 1:2;
ii) maintaining the mixture under conditions sufficient to dissolve at least a portion of the polysaccharide present in the polysaccharide biomass;
iii) reducing the pH of the mixture containing the dissolved polysaccharide to at least about 7;
iv) adding at least one glycoside hydrolase to the mixture having the reduced pH; and
v) maintaining the mixture containing the glycoside hydrolase under conditions sufficient to hydrolyze at least a portion of the dissolved polysaccharide, thereby forming the sugar composition;
wherein the sugar composition contains at least one monosaccharide or oligosaccharide.

Polysaccharide Biomass

The methods of the invention are used for the production of sugar compositions (containing monosaccharides, oligosaccharides, and/or polysaccharides) as chemical or fermentation feedstocks from biomass materials. The feedstocks, in turn, can be used for the production of ethanol, plastics, or other products or intermediates. Biomass can include, but is not limited to, wood resources, municipal solid waste, wastepaper, and crop residues (see, for example, Wiselogel et al., 1995, in Handbook on Bioethanol (Charles E. Wyman, editor), pp. 105-118, Taylor & Francis, Washington D.C.; Wyman, 1994, Bioresource Technology 50: 3-16; Lynd, 1990, Applied Biochemistry and Biotechnology 24/25: 695-719; Mosier et al., 1999, Recent Progress in Bioconversion of Lignocellulosics, in Advances in Biochemical Engineering/Biotechnology, T. Scheper, managing editor, Volume 65, pp. 23-40, Springer-Verlag, New York). Other examples of biomass include, without limitation, crops such as starch crops (e.g., corn, wheat, or barley), sugar crops (e.g., sugarcane, energy cane or sugar beet), forage crops (e.g., grasses, alfalfa, or clover), and oilseed crops (e.g., soybean, sunflower, or safflower); wood products such as trees, shrubs, and wood residues (e.g., sawdust, bark or the like from forest clearings and mills); waste products such as municipal solid waste (MSW; e.g., paper, food and yard wastes, or wood), process waste, and paper sludge; and aquatic plants such as algae, water weeds, water hyacinths, or reeds and rushes. Other examples of biomass include sorghum, rice hulls, rice straw, wheat straw, and other straws.

Accordingly, some embodiments of the invention provide a method for preparing a sugar composition as described above, wherein the polysaccharide biomass comprises cellulose, hemicellulose, lignocellulose, or mixtures thereof. In some embodiments, the polysaccharide biomass comprises lignocellulose.

Biomass materials typically contain a mixture of polysaccharide species. In many instances, the predominant polysaccharide in the primary cell wall of biomass is cellulose, the second most abundant is hemi-cellulose, and the third is pectin. The secondary plant cell wall, produced after the cell has stopped growing, also contains polysaccharides and is strengthened through polymeric lignin covalently cross-linked to hemicellulose.

Cellulose is a homopolymer of anhydrocellobiose and thus a linear β-(1-4)-D-glucan, while hemicelluloses include a variety of sugar subunits, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which helps stabilize the cell wall matrix.

In addition to the polysaccharides described above, polysaccharide biomass typically contains lignin. Lignin is a phenylpropane polymer of monolignol monomers. It is generally found as an integral part of the secondary cell walls of plants and certain types of algae. There are three monolignol monomers, methoxylated to various degrees: p-coumaryl alcohol, coniferyl alcohol, and sinapyl alcohol. These lignols are incorporated into lignin in the form of the phenylpropanoids p-hydroxyphenyl (H), guaiacyl (G), and syringyl (S), respectively. Gymnosperms have a lignin that consists almost entirely of G with small quantities of H. That of dicotyledonous angiosperms is more often than not a mixture of G and S (with very little H), and monocotyledonous lignin is a mixture of all three. Many grasses have mostly G, while some palms have mainly S. All lignins contain small amounts of incomplete or modified monolignols, and other monomers are prominent in non-woody plants. Unlike cellulose and hemicellulose, lignin cannot be depolymerized by hydrolysis. Cleavage of the principal bonds in the lignin polymer generally proceeds through oxidation.

In some embodiments, the polysaccharide biomass is derived from corn stover, corn fiber, hard wood, softwood, cereal straw, switchgrass, *Miscanthus*, rice hulls, municipal solid waste (MSW), industrial organic waste, office paper, or mixtures thereof.

Ionic Liquids

A number of ionic liquids can be used in the methods of the invention. In general, the ionic liquid is suitable for pretreatment of the biomass and compatible with glycoside hydrolases used for saccharification of cellulose and other polysaccharides. The ionic liquids contain a dicarboxylic acid ion paired with cations via electrostatic interactions. In certain embodiments, the ionic liquid used for biomass pretreatment contains one dicarboxylic acid di-anion paired with two cations.

Any suitable dicarboxylic acid can be used in the methods of the invention. In general, the dicarboxylic acid is a $C_{3-16}$ alkane-dioic acid or a $C_{3-16}$ alkene-dioic acid which is branched or unbranched. The dicarboxylic acid can be, for example, a $C_{3-12}$ alkane-dioic acid, a $C_{3-12}$ alkene-dioic acid, a $C_{3-10}$ alkane-dioic acid, a $C_{3-10}$ alkene-dioic acid, a $C_{3-8}$ alkane-dioic acid, a $C_{3-8}$ alkene-dioic acid, a $C_{3-6}$ alkane-dioic acid, a $C_{3-6}$ alkene-dioic acid, a $C_6$ alkane-dioic acid, a $C_6$ alkene-dioic acid, a $C_4$ alkane-dioic acid, or a $C_4$ alkene-dioic acid. The dicarboxylic acids contain two carboxy moieties (i.e., —COOH groups) which can be on any carbon atom. The carbon number designator for a given carboxylic acid (e.g., $C_4$) includes the carbon atoms of the carboxy moieties. The dicarboxylic acid can be substituted with from one to three substituents selected from amino, hydroxy, halo, and oxo. The hydroxyl, halo, amino, and oxy substituents can be on the same carbon atom or on different carbon atoms in the dicarboxylic acid.

In some embodiments, the dicarboxylic acid is selected from adipic acid, aspartic acid, azelaic acid, dodecanedioic acid, fumaric acid, glutamic acid, glutaric acid, maleic acid, malonic acid, pimelic acid, sebacic acid, suberic acid, succinic acid, undecanedioic acid, and mixtures thereof. In some embodiments, the dicarboxylic acid is selected from succinic acid and glutamic acid.

The ionic liquids used in the methods of the invention can contain any suitable cation. Suitable cations include, but are not limited to, ammonium cations and imidazolium cations. Examples of ammonium cations include, but are not limited to, 2-hydroxyethyl-trimethylammonium, benzyldimethyltetradecylammonium, benzyltrimethylammonium, butyltrimethylammonium, choline, diethylmethyl(2-methoxyethyl) ammonium, ethyldimethylpropylammonium, methyltrioctadecylammonium, methyltrioctylammonium, tetrabutylammonium, tetradodecylammonium, tetraethylammonium, tetraheptylammonium, tetrahexadecylammonium, tetrahexylammonium, tetrakis(decyl)ammonium, tetramethylammonium, tetraoctylammonium, tributylmethylammonium, triethylmethylammonium, and tris(2-hydroxyethyl)methylammonium.

The imidazolium cations can be, but are not limited to, 1-alkyl-3-alkylimidazolium cations, wherein an "alkyl" is an alkyl group comprising from 1 to 10 carbon atoms. In some embodiments, the "alkyl" is a methyl group, ethyl group or butyl group. Examples of imidazolium cations include: 1-(2-hydroxyethyl)-3-methylimidazolium; 1-(3-cyanopropyl)-3-methylimidazolium; 1,2,3-trimethylimidazolium; 1,2-dimethyl-3-propylimidazolium; 1,3-bis(cyanomethyl) imidazolium; 1,3-diethoxyimidazolium; 1,3-dihydroxy-2-methylimidazolium; 1,3-dihydroxyimidazolium; 1,3-dimethoxy-2-methylimidazolium; 1,3-dimethoxyimidazolium; 1,3-dimethylimidazolium; 1-allyl-3-methylimidazolium; 1-benzyl-3-methylimidazolium; 1-butyl-2,3-dimethylimidazolium; 1-butyl-3-methylimidazolium (BMIM); 1-decyl-3-methylimidazolium; 1-dodecyl-3-methylimidazolium; 1-ethyl-2,3-dimethylimidazolium (EDIM); 1-ethyl-3-methylimidazolium (EMIM); 1-hexyl-3-methylimidazolium; 1-methyl-3-octylimidazolium; 1-methyl-3-propylimidazolium; 1-methylimidazolium (MIM); and 4-(3-butyl-1-imidazolio)-1-butanesulfonate.

Other cations can be used in the ionic liquids of the present invention, including, but not limited to: pyridinium cations (e.g., N-ethylpyridinium, N-butylpyridinium, and the like); sulfonium cations (e.g., trimethylsulfonium, triethylsulfonium, tributylsulfonium, diethylmethylsulfonium, dimethylpropylsulfonium, dimethylhexylsulfonium, and the like); and phosphonium cations (e.g., tetramethylphosphonium, tetraethylphosphonium, tetrapropylphosphonium, tetrabutylphosphonium, tetraoctylphosphonium, tetraphenylphosphonium, trimethylethylphosphonium, triethylmethylphosphonium, hexyltrimethylphosphonium, trimethyloctylphosphonium, and the like).

In some embodiments, the cation is selected from choline, $(C_{1-18}$ alkyl$)_3NH^+$, $(C_{1-6}$ alkyl$)_x(C_{6-18}$ alkyl$)_yN^+$, $(C_{1-10}$ alkyl$)_z$imidazolium, $(C_{1-10}$ alkyl$)_z$pyrazolium, and mixtures thereof; wherein subscript x and subscript y are each 0, 1, 2, 3, or 4, and the sum of x and y is 4; and wherein each subscript z is 1, 2, or 3.

The cation be, for example, $(C_{1-16}$ alkyl$)_3NH^+$, $(C_{1-12}$ alkyl$)_3NH^+$, $(C_{1-10}$ alkyl$)_3NH^+$, $(C_{1-8}$ alkyl$)_3NH^+$, $(C_{1-6}$ alkyl$)_3NH^+$, $(C_{12-18}$ alkyl$)_3NH^+$, or $(C_{16-18}$ alkyl$)_3NH^+$. The cation be $(C_{1-3}$ alkyl$)_x(C_{6-12}$ alkyl$)_yN^+$ or $(C_{1-2}$ alkyl$)_x(C_{6-8}$ alkyl$)_yN^+$, wherein subscript x and subscript y are each 0, 1, 2, 3, or 4, and the sum of x and y is 4. The cation can be $(C_{1-8}$ alkyl$)_z$ imidazolium, $(C_{1-6}$ alkyl$)_z$imidazolium, $(C_{1-8}$ alkyl$)_z$ pyrazolium, or $(C_{1-6}$ alkyl$)_z$pyrazolium, wherein each subscript z is 1, 2, or 3.

In some embodiments, the cation is selected from 1-ethyl-3-methylimidazolium, 1-butyl-3-methylimidazolium, 1-ethyl-2,3-dimethylimidazolium, tris(2-hydroxyethyl) methylammonium, 1-methylimidazolium, 1,2,4-trimethylpyrazolium, triethylammonium, tributylmethylammonium, hexadecyltrimethylammonium, myristyltrimethylammonium, tridodecylmethylammonium, trimethyloctadecylammonium, and choline. In some embodiments, the cation is choline.

The ionic liquids used in the methods of the invention can be prepared by combining a dicarboxylic acid, or a salt thereof, with a salt containing the cation to be incorporated into the ionic liquid. The dicarboxylic acid and the cation can be combined as solutions in water or in a suitable organic solvent. As a non-limiting example, one equivalent of succinic acid in aqueous solution can be combined with two equivalents of choline hydroxide in aqueous solution. Water can be removed at elevated temperature and/or under reduced pressure. Water-miscible co-solvents, including but not limited to methanol, acetonitrile, acetone, and the like, can be used to precipitate excess anions or cations for removal by centrifugation or filtration. Impurities can be removed by passing the ionic liquid through activated charcoal, polymeric ion-exchange resins, or other decolorizing agents.

In general, the molar ratio of the dicarboxylic acid anions in the ionic liquid solution to the cations in the ionic liquid solution will be sufficient to provide a solution pH of at least about 7. In certain embodiments, the molar ratio of the dicarboxylic acid anion to the cation is at least about 1:2. The molar ratio of the dicarboxylic acid anion to the cation can be, for example, at least 1:1.8, or at least 1:1.9; or at least 1:2, or at least 1:2.1 or at least 1:2.2. When the mixture of the dicarboxylic acid and the salt is made in aqueous solution, the pH of the resulting ionic liquid solution will be basic. In general, the pH of the ionic liquid solution is above 7. The pH of the ionic liquid solution can be, for example, at least 7, at least 7.5, at least 8, at least 8.5, at least 9, at least 9.5, at least 10, at least 10.5, at least 11, at least 11.5, at least 12, or at least 12.5. In certain embodiments, one equivalent of a dicarboxylic acid is combined with two equivalents of a salt containing a cation and a basic anion. As a non-limiting example, combination of one equivalent of succinic acid with two equivalents of choline hydroxide in aqueous solution will result in an ionic liquid solution having a pH of about 11. One of skill in the art will appreciate that the pH of the ionic liquid solution will vary depending on the particular dicarboxylic acid and cation used, the ratio of the dicarboxylic acid and the cation, and their absolute concentrations.

As described in more detail below, the pH of mixture containing the ionic liquid solution is reduced after the pretreatment step so that mixture is compatible with enzymes, such as cellulases, used to break down the pretreated biomass. In certain embodiments, the pH is reduced by adding the same dicarboxylic acid that is present in the ionic liquid. Accordingly, in some embodiments an ionic liquid solution having a pH of at least about 10 is obtained by combining one equivalent of a dicarboxylic acid with two equivalents of a salt containing a cation; the pH of the ionic liquid solution is then reduced to below about 7 via addition of a second equivalent of the carboxylic acid prior to the introduction of enzymes such as glycoside hydrolases.

In some embodiments the ionic liquid solution having a pH of at least about 10 is obtained by combining one equivalent of succinic acid with two equivalents of choline hydroxide. After pretreatment of the polysaccharide biomass, the pH of the ionic liquid solution is then reduced to below about 7 via addition of a second equivalent of succinic acid prior to the introduction of enzymes such as glycoside hydrolases.

In some embodiments the ionic liquid solution having a pH of at least about 10 is obtained by combining one equivalent of glutamic acid with two equivalents of choline hydroxide. After pretreatment of the polysaccharide biomass, the pH of the ionic liquid solution is then reduced to below about 7 via addition of a second equivalent of glutamic acid prior to the introduction of enzymes such as glycoside hydrolases.

The pH of an ionic liquid solution can be raised or lowered as necessary by adding bases, such as sodium hydroxide or potassium hydroxide, and acids, such as hydrochloric acid or sulfuric acid, to the ionic liquid solution. As a non-limiting example, combination of one equivalent of succinic acid with one equivalent of choline hydroxide in aqueous solution followed by the addition of potassium hydroxide can provide an ionic liquid having a pH of about 11.

The ionic liquid solution can contain any suitable amount of water. In general, the ionic liquid solutions used in the methods of the invention contain from about 0.1% water to about 95% water by weight of the ionic liquid solution. An ionic liquid solution can contain, for example, from about 5% to about 90% water, or from about 10% to about 80% water, or from about 20% to about 60% water, or from about 30% to about 50% water, or from about 0.1 to about 50% water, or from about 5% to about 45% water, or from about 10% to about 40% water, or from about 15% to about 35% water, or from about 20% to about 30% water by weight of the ionic liquid solution. The ionic liquid solution can contain about 0.1, 1, 5, 10, 15, 20, 25, 30, 35, 40, 45, 50, 55, 60, 65, 70, 71, 72, 73, 74, 75, 76, 77, 78, 79, 80, 81, 82, 83, 84, 85, 86, 87, 88, 89, 90, 91, 92, 93, 94, or about 95% water by weight of the ionic liquid solution.

In certain embodiments, the ionic liquid solution contains from about 70% (w/w) to about 95% (w/w) water. The ionic liquid solution can contain from about 70% to about 75% water, or from about 75% to about 80% water, or from about 80% to about 85% water, or from about 85% to about 90% water, or from about 90% to about 95% water by weight of the ionic liquid solution. The ionic liquid solution can contain from about 70% to about 90% water, or from about 72% to about 85% water, or from about 73% to about 80% water by weight of the ionic liquid solution. The ionic liquid solution can contain from about 70% to about 95% water, or from about 80% to about 93% water, or from about 85% to about 92% water by weight of the ionic liquid solution. In such embodiments, the ionic liquid solution will contain from about 30% to about 5% (w/w) ionic liquid. The ionic liquid solution can contain from about 25% to about 30% ionic liquid, or from about 20% to about 25% ionic liquid, or from about 15% to about 20% ionic liquid, or from about 10% to about 15% ionic liquid, or from about 5% to about 10% ionic liquid by weight of the ionic liquid solution. The ionic liquid solution can contain from about 10% to about 30% ionic liquid, or from about 15% to about 28% ionic liquid, or from about 20% to about 27% ionic liquid by weight of the ionic liquid solution. The ionic liquid solution can contain from about 5% to about 30% ionic liquid, or from about 7% to about 20% ionic liquid, or from about 8% to about 15% ionic liquid by weight of the ionic liquid solution.

Other amounts of water and ionic liquid can be used in the methods of the invention, depending in part on factors such as the type of biomass material to be treated and the particular cations and carboxylic acid anions to be included in the ionic liquid.

In some embodiments, the ionic liquid solution contains:
about 70-95% (w/w) water; and
about 5-30% [dicarboxylic acid anion][cation] (w/w).
In some embodiments, the ionic liquid solution contains:
about 70-95% (w/w) water; and
about 5-30% 1:2 [dicarboxylic acid anion][cation] (w/w).
In some embodiments, the ionic liquid solution contains:
about 70-95% (w/w) water; and
about 5-30% 1:2 [glutamate di-anion][cation] (w/w).
In some embodiments, the ionic liquid solution contains:
about 70-95% (w/w) water; and
about 5-30% 1:2 [aspartate di-anion][cation] (w/w).
In some embodiments, the ionic liquid solution contains:
about 70-95% (w/w) water; and
about 5-30% 1:2 [succinate di-anion][cation] (w/w).
In some embodiments, the ionic liquid solution contains:
about 70-95% (w/w) water; and
about 5-30% dicholine glutamate (w/w).
In some embodiments, the ionic liquid solution contains:
about 70-95% (w/w) water; and
about 5-30% dicholine succinate (w/w).
In some embodiments, the ionic liquid solution contains:
about 75-90% (w/w) water; and
about 10-25% [dicarboxylic acid anion][cation] (w/w).
In some embodiments, the ionic liquid solution contains:
about 75-90% (w/w) water; and
about 10-25% 1:2 [dicarboxylic acid anion][cation] (w/w).
In some embodiments, the ionic liquid solution contains:
about 75-90% (w/w) water; and
about 10-25% 1:2 [glutamate di-anion][cation] (w/w).
In some embodiments, the ionic liquid solution contains:
about 75-90% (w/w) water; and
about 10-25% 1:2 [aspartate di-anion][cation] (w/w).
In some embodiments, the ionic liquid solution contains:
about 75-90% (w/w) water; and
about 10-25% 1:2 [succinate di-anion][cation] (w/w).
In some embodiments, the ionic liquid solution contains:
about 75-90% (w/w) water; and
about 10-25% dicholine glutamate (w/w).
In some embodiments, the ionic liquid solution contains:
about 75-90% (w/w) water; and
about 10-25% dicholine succinate (w/w).
In some embodiments, the ionic liquid solution contains:
75-90% (w/w) water; and
10-25% [dicarboxylic acid anion][cation] (w/w).
In some embodiments, the ionic liquid solution contains:
75-90% (w/w) water; and
10-25% 1:2 [dicarboxylic acid anion][cation] (w/w).
In some embodiments, the ionic liquid solution contains:
75-90% (w/w) water; and
10-25% 1:2 [glutamate di-anion][cation] (w/w).

In some embodiments, the ionic liquid solution contains:
75-90% (w/w) water; and
10-25% 1:2 [aspartate di-anion][cation] (w/w).
In some embodiments, the ionic liquid solution contains:
75-90% (w/w) water; and
10-25% 1:2 [succinate di-anion][cation] (w/w).
In some embodiments, the ionic liquid solution contains:
75-90% (w/w) water; and
10-25% dicholine glutamate (w/w).
In some embodiments, the ionic liquid solution contains:
75-90% (w/w) water; and
10-25% dicholine succinate (w/w).

The pretreatment mixture can contain any suitable amount of polysaccharide biomass. In general, the pretreatment mixture contains up to about 50% biomass by weight of the pretreatment mixture. The pretreatment mixture can contain, for example, from about 0.1 to about 50% biomass, or from about 5% to about 45% biomass, or from about 10% to about 40% biomass, or from about 15% to about 35% biomass, or from about 20% to about 30% biomass, or from about 5% to about 40% biomass, or from about 5% to about 30% biomass, or from about 5% to about 20% biomass, or from about 5% to about 10% biomass by weight of the pretreatment mixture. The pretreatment mixture can contain about 1, 5, 10, 15, 20, 25, 30, 35, 40, 45, or 50% biomass by weight of the pretreatment mixture. In some embodiments, the mixture includes from about 5% (w/w) to about 30% (w/w) polysaccharide biomass. Other amounts of biomass can be used in the methods of the invention, depending in part on factors such as the type of biomass material and the particular ionic liquid used in the method.

Biomass Pretreatment

Pretreatment of the polysaccharide biomass in the ionic liquid solution can be conducted for any suitable length of time at any suitable temperature and pressure. In general, pretreatment is conducted for anywhere from a few minutes to several hours. Pretreatment can be conducted, for example, for about five minutes, or about 10 minutes, or about 30 minutes, or about 60 minutes. Pretreatment can be conducted for about 1, 1.5, 2, 2.5, 3, 3.5, 4, 4.5, 5, 5.5, 6, 9, 12, 15, 18, 21, 24, 36, 48, 60, or about 72 hours. Pretreatment is generally conducted at a temperature ranging from about 20° C. to about 200° C. Pretreatment can be conducted, for example, at a temperature ranging from about 20° C. to about 100° C., or from about 40° C. to about 80° C., or from about 100° C. to about 200° C., or from about 120° C. to about 180° C., or from about 140° C. to about 160° C., or from about 40° C. to about 180° C., or from about 60° C. to about 160° C., or from about 80° C. to about 140° C., or from about 100 to about 120° C. Pretreatment can be conducted at about 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or about 200° C. for at least about 0.5, 1, 3, 6, 9, 12, or 16 hours. Pretreatment can be conducted at atmospheric pressure or elevated pressures. Pretreatment can be conducted, for example, at a pressure (Pg) ranging from about 14 psi to about 4000 psi, or from about 14 psi to about 3500 psi, or from about 14 psi to about 2500 psi, or from about 14 psi to about 1500 psi. In certain embodiments, the pretreatment is conducted at around atmospheric pressure (i.e., 14.696 psi).

In some embodiments, the invention provides a method for preparing a sugar composition as described above wherein step ii) includes maintaining the mixture of step i) at a temperature of at least about 100° C. for at least about 30 minutes.

Biomass Saccharification

Following pretreatment of the polysaccharide biomass, the pH of the mixture containing the dissolved polysaccharide and the ionic liquid solution is reduced to a level that is suitable for enzymatic hydrolysis of the polysaccharide by one or more glycoside hydrolases. In general, the pH of mixture is reduced to at most about 7. The pH of the mixture can be reduced, for example, to less than 7, less than 6.5, less than 6, less than 5.5, or less than 5. In certain embodiments, the pH of the mixture is reduced to a pH of from about 5 to about 6.

The pH of the mixture containing the dissolved polysaccharide can be reduced by adding an acid to the mixture. Any suitable acid can be used to reduce the pH. Suitable acids include, but are not limited to, hydrochloric acid, sulfuric acid, nitric acid, acetic acid, citric acid, formic acid, and the like. In certain embodiments, the acid used for reducing the pH of the mixture containing the dissolved polysaccharide is the same dicarboxylic acid that is present in the ionic liquid. In certain such embodiments, the mixture containing the dissolved polysaccharide and the ionic liquid solution is combined with one molar equivalent of the dicarboxylic acid (with respect to the amount of the dicarboxylic acid present in the ionic liquid). As a non-limiting example, combination of one equivalent of succinic acid with a mixture containing dissolved polysaccharide and dicholine succinate will reduce the pH of the mixture to between about 5 and about 6. Further adjustments to the pH can be made by adding further amounts of acid (e.g., hydrochloric acid) to the mixture as necessary. One of skill in the art will appreciate that the pH of the mixture containing the dissolved polysaccharide can be adjusted to maximize the activity of an enzyme, or a mixture of enzymes, e.g., one or more glycoside hydrolases, used in the subsequent hydrolysis step. The particular pH will depend in part on factors including, but not limited to, the specific glycoside hydrolase(s) and the amount of ionic liquid in the mixture.

Accordingly, some embodiments of the invention provide a method for preparing a sugar composition as described above wherein step iii) includes adding an acid to the mixture resulting from step ii). In some such embodiments, the acid used in step iii) is the same dicarboxylic acid used in step i). In some such embodiments, the molar amount of acid in step iii) is equal to the molar amount of acid in step i).

The methods of the invention generally include adding on or more enzymes that break down polysaccharide biomass into smaller components. Typically, the pretreated biomass is subjected to the action of one, or multiple, enzyme activities selected from a protease, a lipase, a cellulase, an amylase, a glucano-hydrolase, a pectinase, a xylanase, a ferulic acid esterase, and a mannanase. The pretreated biomass may also be treated with other enzymes, e.g., hemicellulases, that are used for the degradation of biomass.

In some embodiments, the glycoside hydrolase is selected from an endoglucanase, an exoglucanase, a β-glucosidase, a xylanase, and mixtures thereof. In some embodiments, one or more cellulases are added to the pretreated biomass present in the ionic liquid mixture in which the pH has been reduced, e.g., to at least about 7, following treatment at a high pH.

A "cellulase" as used herein is a glycoside hydrolase enzyme that hydrolyzes cellulose (β-1,4-glucan or β-D-glucosidic linkages) resulting in the formation of glucose, cellobiose, cellooligosaccharides, and the like. In the context of the present invention, cellulases include endoglucanases; exoglucanases or cellobiohydrolases; and β-glucosidases.

Endoglucanases (EC 3.2.1.4) including endo-1,4-β-glucanases or 1,4-β-D-glucan-4-glucanohydrolases, act randomly on soluble and insoluble 1,4-β-glucan substrates. Exoglucanases (exo-1,4-β-D-glucanases, e.g., the 1,4-β-D-glucan glucohydrolases; EC 3.2.1.74) liberate D-glucose from 1,4-β-D-glucans and hydrolyze D-cellobiose slowly. Cellobiohydrolases (1,4-β-D-glucan cellobiohydrolases, EC 3.2.1.91) liberate D-cellobiose from 1,4-β-glucans. β-Glucosidases ([β]-D-glucoside glucohydrolase; β-D-glucosidases; EC 3.2.1.21) act to release D-glucose units from cellobiose and soluble cellodextrins, as well as an array of glycosides. Endoglucanases act mainly on the amorphous parts of the cellulose fiber, whereas cellobiohydrolases are also able to degrade crystalline cellulose.

A combination of two or more cellulases can be used in the methods of the invention. Cellulases act in concert to catalyze the hydrolysis of cellulose-containing substrates. For example, endoglucanases break internal bonds and disrupt the crystalline structure of cellulose, exposing individual cellulose polysaccharide chains ("glucans"). Cellobiohydrolases incrementally shorten the glucan molecules, releasing mainly cellobiose units (a water-soluble β-1,4-linked dimer of glucose) as well as glucose, cellotriose, and cellotetrose. β-glucosidases split the cellobiose into glucose monomers. The cellulase can be a thermostable cellulase. In certain embodiments the glycoside hydrolase, such as a cellulase, is selected such that it can perform optimally in the presence of ionic liquid.

A xylanase and/or a "mannanase" may also be employed in the saccharification of pretreated biomass. A "xylanase" is a glycoside hydrolase enzyme that catalyzes the endohydrolysis of 1,4-β-D-xylosidic linkages in xylans. Xylanases include enzymes classified as a 1,4-β-D-xylan-xylohydrolase (E.C. 3.2.1.8).

A "mannanase" is a glycoside hydrolase that hydrolyzes 1,4-β-D-mannosidic linkages in mannans, galactomannans and/or glucomannans. "Mannanase activity" refers to hydrolysis of 1,4-β-D-mannosidic linkages in mannans, galactomannans and/or glucomannans. Mannases include enzymes classified as EC 3.2.1.78.

Cellulases suitable for use in the present invention are commercially available from, for example, Genencor (USA) and Novozymes (Europe). For instance, Novozyme has a number of different enzymes and enzyme complexes that are specifically designed to be useful for the hydrolysis of lignocellulosic materials. Examples include, but are not limited to, the following: NS50013, which is a cellulase; NS50010, which is a β-glucosidase; NS22086, which is a cellulase complex; NS22086, which is a xylanase; NS22118, which is β-glucosidase; NS22119, which is an enzyme complex of carbohydrases, including arabinase, β-glucanase, cellulase, hemicellulase, pectinase, and xylanase; NS22002, which is a mixture of β-glucanase and xylanase; and NS22035, which is a glucoamylase. In addition, suitable thermostable cellulases are disclosed in PCT International Publication No. WO 2010/124266, the teachings of which are incorporated herein by reference. Other hydrolases suitable for hydrolyzing the pretreated biomass, i.e., the lignocellulosic material, will be known to those of skill in the art. See e.g., Viikari et al., *Adv. Biochem. Eng. Biotechnol.*, 108:121-45, 2007; and U.S. Patent Application Nos. 2009/0061484; US 2008/0057541; and US 2009/0209009, which are incorporated by reference.

Any suitable amount of enzyme or enzyme mixture, e.g., glycoside hydrolase or mixture of glycoside hydrolases, can be used in the methods of the invention. In general a sub-stoichiometric amount of the glycoside hydrolase, with respect to the dissolved polysaccharide, is used. The amount of glycoside hydrolase can be expressed as activity units. Alternatively, the amount of the glycoside hydrolase used in the methods of the invention can be expressed relative to the amount of biomass treated in the pretreatment step. For example, the hydrolysis mixture can contain a glycoside hydrolase (or a mixture of glycoside hydrolases) in an amount ranging from about 0.01 to about 10% (w/w), with respect to the amount of biomass used in the pretreatment step. Thus, for example, when the method is conducted using 1 kg of biomass, for example, the hydrolysis step can be conducted with a glycoside hydrolase or a mixture of glycoside hydrolases in an amount ranging from about 100 mg to about 100 g. Those of skill in the art will appreciate that the amount of glycoside hydrolase or mixture of enzymes used in the methods of the invention will depend in part on factors including, but not limited to, the particular enzyme used, the nature of the biomass source, and the extent of the pretreatment step.

The enzymatic hydrolysis step can be conducted for any length of time at any suitable temperature. The enzymatic hydrolysis step can be conducted, for example, for about 2, 5, 10, 15, 30, 45, or 60 minutes. The enzymatic hydrolysis step can be conducted for about 1, 1.5, 2, 2.5, 3, 3.5, 4, 4.5, 5, 5.5, 6, 9, 12, 15, 18, 21, 24, 30, 36, 42, 48, or 72 hours. Enzymatic hydrolysis is generally conducted at a temperature ranging from about 20° C. to about 60° C. Enzymatic hydrolysis can be conducted, for example, at a temperature ranging from about 20° C. to about 40° C., or from about 40° C. to about 60° C. Enzymatic hydrolysis can be conducted at about 25° C., about 37° C., or about 55° C. for at least about 10, 20, 30, 60, or 90 minutes or for at least about 2, 3, 4, 5, 6, 7, 8, 9, 10, 11, 12, 24, 48, or 72 hours.

Sugar Compositions

The methods of the invention provide sugar compositions containing one or monosaccharides and/or oligosaccharides. Monosaccharides present in the sugar compositions can include, but are not limited to, fucose, arabinose, rhamnose, galactose, mannose, xylose, glucose, glucuronic acid, and galacturonic acid. The oligosaccharides in the sugar compositions contain monosaccharide subunits (e.g., fucose, arabinose, rhamnose, galactose, mannose, xylose, glucose, glucuronic acid, and galacturonic acid) linked together via glycosidic bonds. Typically, between about 10% and about 100% conversion of the polysaccharide biomass to sugars results from the methods of the invention. Thus, e.g., processing of 1 kg of polysaccharide biomass according to the methods of the invention can yield from about from about 110 g to about 1100 g of the constituent monosaccharides and oligosaccharides in the final sugar compositions. For example, processing of 1 kg of switchgrass according to the methods of the invention can yield sugar compositions containing from about 0.1 g to about 350 g of glucose and from about 0.1 g to about 210 g to xylose. One of skill in the art will appreciate that the components and the yield of the sugar composition will depend, in part, on the specific source of the biomass and the specific conditions that are used for pretreatment and hydrolysis.

In some embodiments, the method includes:
i) forming a mixture including switchgrass and an ionic liquid solution,
   wherein the ionic liquid solution contains about 10-25% (w/w) dicholine glutamate and about 75-90% (w/w) water, and
   wherein the pH of the mixture is at least about 11;
ii) maintaining the mixture at about 120° C. for about three hours, thereby dissolving the lignocellulose present in the switchgrass;

iii) adding glutamic acid to the mixture containing the dissolved lignocellulose, wherein the amount of glutamic acid is equal to the amount of glutamate in step i);
iv) adding at least one glycoside hydrolase to the mixture resulting from step iii); and
v) maintaining the mixture containing the glycoside hydrolase at about 50° C. for about 72 hours, thereby forming the sugar composition;

wherein the sugar composition contains glucose.

Fermentation

The sugar compositions produced via the methods of the invention can, in turn, be used as carbon sources for host cells to produce useful organic compounds such as biofuels. Examples of such products include, but are not limited to, alcohols (e.g., ethanol, methanol, butanol); organic acids (e.g., citric acid, acetic acid, itaconic acid, lactic acid, gluconic acid); ketones (e.g., acetone); amino acids (e.g., glutamic acid); gases (e.g., $H_2$ and $CO_2$); antibiotics (e.g., penicillin and tetracycline); enzymes; vitamins (e.g., riboflavin, B12, β-carotene); fatty acids and fatty acid derivatives (as described, e.g., in PCT/US2008/068833); isoprenyl alkanoates (as described, e.g., PCT/US2008/068756, methyl butenol (as described, e.g., PCT/US2008/068831; fatty acid esters (as described, e.g., in PCT/US2010/033299), isoprenoid-based alternative diesel fuel (as described, e.g., in PCT/US2011/059784; a polyketide synthesized by a polyketide synthase, such as a diacid (see, e.g., PCT/US2011/061900), biofuels (see, e.g., PCT/US2009/042132) and alpha-olefins (see, e.g., PCT/US2011/053787).

Accordingly, some embodiments of the invention provide a method for converting a sugar composition to a fermentation product, wherein the method includes fermenting a mixture containing a sugar composition prepared according to the methods described above.

In certain embodiments, fermenting the sugar composition is conducted without removing the ionic liquid. That is, the fermentation step is conducted in the mixture containing the ionic liquid and the fermentable sugars resulting from step v) of the method described above (i.e., a crude sugar composition). In such embodiments, fermenting the sugar composition comprises adding a fermentation microorganism to the mixture containing the sugar composition and the ionic liquid. The mixture containing the sugar composition and the ionic liquid can be diluted (e.g., with growth medium such as EZ-dex growth medium, a buffer, or combinations thereof) prior to addition of the microorganisms so as to maintain the viability of the microorganisms during the fermentation process. In some embodiments, the mixture is diluted such that the concentration of the ionic liquid is less than about 15% (w/w). For example, the mixture can be diluted such that the concentration of the ionic liquid is less than about 15, 14, 13, 12, 11, 10, 9, 8, 7, 6, 5, 4, 3, 2, or 1% (w/w). The mixture containing the sugar composition and the ionic liquid can be supplemented by addition of additional sugars such as additional glucose or additional xylose.

Organisms employed for fermentation may be wild-type organisms or may be genetically modified. Such organisms are well known and include bacteria, yeast, microalgae, and filamentous fungi. In some embodiments, the yeast is a *Saccharomyces* sp. e.g., *Saccharomyces cerevisiae* or *Saccharomyces uvarum*. Other yeast may also be employed, e.g., *Kluyveromyces*, such as *Kluyveromyces marxianus*, *Kluyveromyces lactis* or *Kluyveromyces fragilis*; *Candida*, such as *Candida pseudotropicalis* or *Candida brassicae*; a *Hansenula*, *Pichia*, such as *Pichia pastoris*, *Saccharomyces*, *Schizosaccharomyces*, such as *Schizosaccharomyces pombe*, or *Yarrowia* sp. Examples of fermenting bacteria that may be used include *E. coli*, *Klebsiellan* sp., *Bacillus* sp., *Clostridium* sp., *Zymomonas* sp. and others (for example, *Bacillus coagulans*, *Clostridium acetobutylicum*, *Clostridium thermocellum*, *Clostridium phytofermentans*, *Geobacillus* sp., *Thermoanaerobacter saccharolyticum*, and *Zymomonas mobilis*). Examples of filamentus fungi include *Aspergillus* sp., *Trichoderma* sp., *Myceliopthera* sp., and *Neurospora* sp.

Examples of products that can be obtained from microorganisms in the fermentation step of the method include, but are not limited to: ethanol obtained from *Saccharomyces*, *Schizosaccharomyces*, *Saccharomycodes*, *Torulopsis*, *Kluyveromyces*, *Zymomonas mobilis*, or *E. coli*; tartaric acid obtained from Lactobacilli; itaconic acid obtained from *Aspergillus terreus* or *Aspergillus itaconicus*; succinic acid obtained from *Actinobacillus* sp. 130Z, *Anaerobiospirillum succiniproducens*, *Actinobacillus succinogenes*, or *E. coli*; hydroxypropionic acid obtained from *Lactobacillus delbrückii*, *L. leichmannii*, or *Sporolactobacillus inulinus*; propionic acid obtained from *Propionibacterium* or *Clostridium propionicum*; citric acid obtained from an *Aspergillus* sp., such as *Aspergillus niger* or *Aspergillus wentii*; aconitic acid obtained from *Aspergillus niger* or *Aspergillus wentii*; malic acid obtained from *Aspergilli*, *A. niger*, *A. oryzae*, or *Corynebacterium*; gluconic acid obtained from *Aspergilli*; butyric acid obtained from *Clostridium*; lactic acid obtained from *Lactobacillus*; eicosapentaenic acid obtained from *Mortiella*, *Phytium*, *Rhodopseudomonas*, or *Shewanella* spp.; propanediol obtained from *E. coli*; butanediol obtained from *Enterobacter aerogenes*, *Bacillus subtilis*, or *Klebsiella oxytoca*; butanol obtained from *Clostridium* spp.; glycerol obtained from *Saccharomyces rouxii*; mannitol obtained from *Aspergillus candida* or *Torulopsis mannitofaciens*; acetone obtained from *Clostridium*; and gibberellic acid obtained from *Gibberella fujikuroi*.

In some embodiments, *E. coli* or a yeast, such as *Saccharomyces cerevisiae* is used for fermenting the sugar composition in a fermentation conducted without removing the ionic liquid. In some embodiments, fermenting the sugar composition includes producing isopentenol or a bisabolene. In some embodiments, the bisabolene is (E)-1-methyl-4-(6-methylhepta-2,5-dien-2-yl)cyclohex-1-ene; (S)-1-methyl-4-(6-methylhepta-1,5-dien-2-yl)cyclohex-1-ene; (Z)-1-methyl-4-(6-methylhept-5-en-2-ylidene)cyclohex-1-ene; or a mixture thereof.

In certain embodiments, the fermentation step includes extractive fermentation, wherein an extraction solvent is introduced directly into the fermentation mixture so as to remove the product from the fermentation medium as the product is being formed. Any suitable extraction solvent can be used in the methods of the invention. Suitable extraction solvents include, but are not limited to, oleyl alcohol, n-dodecanol, isoamyl acetate, isooctyl alcohol, nonanoic acid, n-butyl acetate, dibutyl ether, and dibutyl oxalate. The properties of the extraction solvent can be chosen so that the extraction solvent separates easily from the fermentation medium for removal from an apparatus such as a fermentor. The extraction solvent can also be replenished, so that the extraction process may be carried out continuously. The extractant containing the product can be removed from the fermentor and treated to separate the product from the extractant. The extractant can then be recycled to the fermentor for the extraction of further product.

As a non-limiting example, the process can be carried out in a continuous stirred tank fermentor in which the microorganism cells are freely suspended. In such an apparatus, for steady state operation, the input rate of fresh substrate solution (known as the dilution rate, i.e., the input flow rate divided by the volume of the fermentor) can be set such that the rate of cell removal in the outflowing medium is equal to the rate of cell production in the fermentor. In this way, the microorganism cell population remains substantially constant.

The extraction solvents disclosed herein may also be used with batchwise fermentation, or fed-batch fermentation or immobilized cell fermentation. Alternatively, downstream extraction can be conducted in a separate step. In such a process, the liquid-liquid extraction of the product is carried out on fermentation medium removed from the fermentor. After separation of the fermentation medium from the extractant/product solution, the medium may be recycled to the fermentor, discarded or treated for the removal of any remaining product.

During the extraction step, the extractant is preferably brought into intimate contact with the aqueous medium in order to promote rapid and complete partition of the product. For example, in the case of in situ extraction, the extractant may be introduced in small streams at the bottom of the fermentor and allowed to rise to the surface to form a continuous surface layer.

After separation of the extractant/product solution from the fermentation medium, the product can be removed from the extractant by any suitable means and, as mentioned above, the extractant may then be recovered and reused for further product extraction. For example, the extractant/product solution may be distilled in order to separate the product from the extractant. As an alternative to distillation, the product may be separated from the extractant by stripping with air or $CO_2$, followed by product condensation, or by any other suitable method. Other separation techniques including, but not limited to, distillation, azeotropic distillation, membrane separation, and adsorption onto solid adsorbents are known to those of skill in the art and can be used to separate the fermentation medium from the fermentation products [see, for example, Huang et al. 2008. *Separation and Purification Technology* 62: 1-21].

Ionic Liquid Recycling

Figure 7:
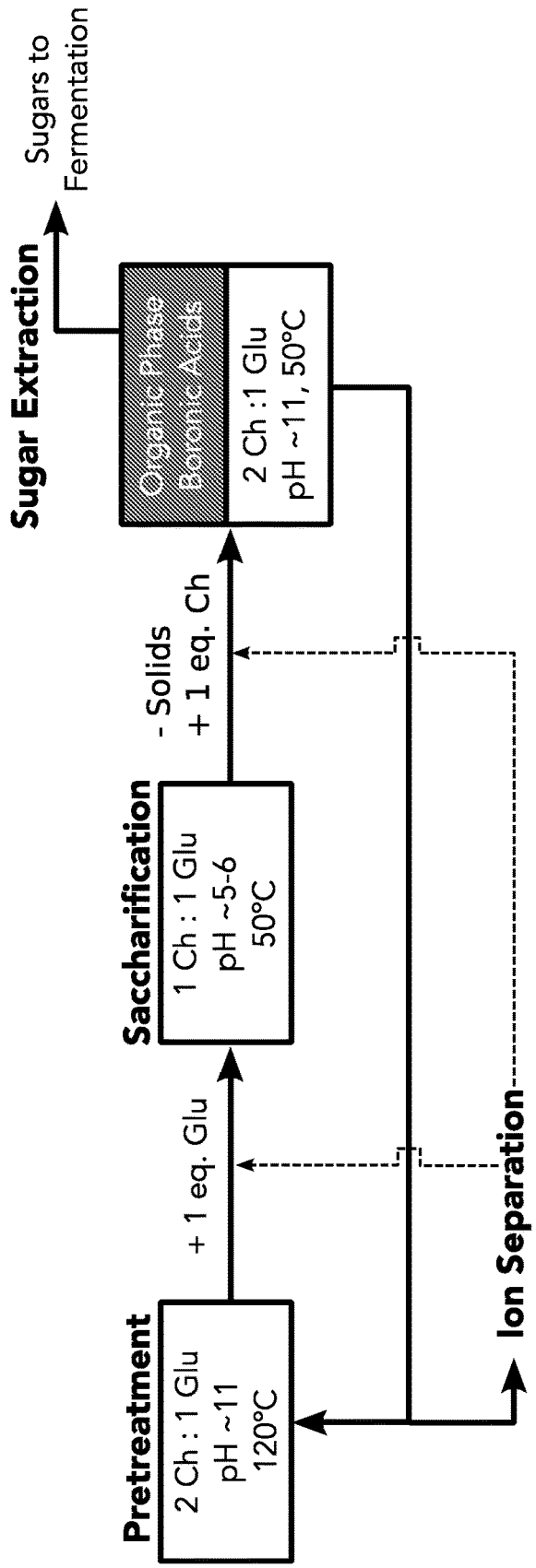
FIG. 7 shows a schematic representation of a process including pretreatment and saccharification of biomass, including extraction of sugars for use in fermentation and recycling of ionic liquids.

The methods of the invention allow for simple recycling of the ionic liquid from one form to another for re-use. This is particularly true for embodiments wherein the same acid (e.g., succinic acid) is used in the pretreatment step and the pH reduction step. An exemplary process employing choline glutamate is shown in FIG. 7. The pretreatment step is performed in the basic stoichiometry, and then the solution is acidified for the enzymatic hydrolysis step. After the hydrolysis, the soluble sugars can be removed by any of the previously reported methods. For example, if a liquid-liquid extraction with boronic acids is used, the solution can be 'switched' back to the basic form first, which matches the conditions required for efficient extraction [Brennan, et al. 2010. *BioEnergy Research* 3: 123-33; Shi, et al. 2013. *Green Chemistry* 15: 2579-89]. After extraction, the IL-phase can be recycled to pretreat another batch of biomass. Alternatively, the hydrolysate can be fed directly into the fermentation step. In certain embodiments, *E. coli*, or a yeast, e.g., *S. cerevisiae*, or other microorganisms can tolerate high concentrations of the hydrolysate produced by this process, limiting the dilution required.

Several parameters have been identified as keys for ushering in the use of an ionic liquid process: ionic liquid price, ion availability, recycled fraction, and IL/biomass use ratio. Others have recently shown that ILs can be produced from inexpensive staring materials like triethylamine and sulfuric acid. See, Chen et al. *Green Chemistry* 16, 3098-3106 (2014). Like those "cheap" ionic liquids, the succinate- and glutamate-based ionic liquids utilize inexpensive ions already produced in large enough quantities to start a commercial-scale process. The choline glutamate process makes significant process toward price and loading. Based on the bulk price for both choline and glutamate, we estimate that an ionic liquid could be produced on the order of ~$1/kg. This price is an order of magnitude lower than previous best-case scenarios for [Em][Ac] and is on par with operating cost estimates for dilute acid processes. See, Klein-Marcuschamer, et al. *Biofuels, Bioproducts and Biorefining* 5, 562-569 (2011). As explained in more detail below, a non-evolved *E. coli* strain can tolerate high concentrations of the hydrolysate/IL streams produced by this process limiting the dilution required. See, FIG. 5. Going forward, if evolved or adapted fermentation strains are utilized, the ILs used in the same concentration throughout the process could further reduce or eliminate the need for energy intensive water removal steps. Previous one-pot ionic liquid processes utilizing boronic acids have a major cost in acid and base used for organic-phase sugar extraction. See, Konda, et al. *Biotechnol Biofuels* 7, (2014). If this step is removed and fermentation is performed in the presence of the ionic liquid, the one-pot process eliminates other costly process steps.

The biomass input, glucose and xylose output, and the insoluble lignin/ash output can be measured for the methods of the invention, and a biomass mass balance for the pretreatment and saccharification steps can be constructed from these streams. Nearly 76% of the original biomass leaves the reactor in the liquid stream.

IV. Examples

Example 1. Ionic Liquid Preparation

All starting chemicals were purchased from Sigma Aldrich. Choline succinate ([Ch][Sc]), (choline)$_2$ succinate (2[Ch][Sc]), choline glutamate ([Ch][Glu]), and (choline)$_2$ glutamate (2[Ch][Glu]) were each synthesized by combining choline hydroxide and the free acid of the respective anion in water. Reactions were allowed to proceed at room temperature for 15 minutes, and then the ionic liquid solution was passed over activated carbon to remove any colored organic impurities. No further purifications were performed to keep the synthesis of the ionic liquids as simple as possible. The composition of the ionic liquid was confirmed by NMR. For tested conditions above 40 wt % ionic liquid, water was removed in a vacuum centrifugal concentrator at 65° C.

Example 2. Cellulase Stability in Ionic Liquids

Enzyme stability was monitored by residual activity measurements. Ctec2 was diluted 200-fold into nine ionic liquid or buffer solutions at concentrations from 1-20 wt %. Each enzyme solution was then divided into 18 wells in a thin-walled PCR plate and incubated in thermal cyclers (Applied Biosystems, Veriti) at temperatures from 38-80° C. for 30 minutes. Aliquots of the incubated enzymes were assayed for residual activity in either 0.5% carboxymethylcellulose (CMC), 1 mM paranitrophenol-cellobiose (PNPC), or 1 mM paranitrophenol-glucopyranoside (PNPG) in 50 mM sodium succinate, pH 5.2 buffer and incubated at 50° C. for 30, 10, or 5 minutes, respectively. CMC reaction end-points were analyzed by DNS assay to detect reducing sugars. The end-points of the paranitrophenol reactions were measured by absorbance at 405 nm. $T_{50}^{30}$ values were determined by the midpoint of a linear interpolation of the transition region. Error was estimated by replication of both the incubation and activity measurement steps. Some solution conditions produced clearly bi-modal inactivation curves; in these cases the larger of the two transitions was reported.

FIG. 1 shows that the stability of Ctec2 remains in various ionic liquids.

Stability was measured as the temperature at which enzyme activity is reduced by 50% ($T_{50}$) following a 30-minute pre-incubation at temperatures ranging from 38 to 80° C. ($T_{50}^{30min}$). The effects of the ionic liquid on stability were monitored as the change in ($T_{50}^{30}$), after pre-incubation in the IL at concentrations of 5, 10, 15 and 20%. To capture the stability differences for several different enzyme classes in the multicomponent commercial enzyme mixture, the $T_{50}^{30}$ was measured on three different representative substrates: carboxymethylcellulose (CMC), 4-Nitrophenyl β-D-glucopyranoside (PNP-glucopyranoside) and 4-Nitrophenyl β-D-cellobiose (PNP-cellobiose).

Figure 1B:
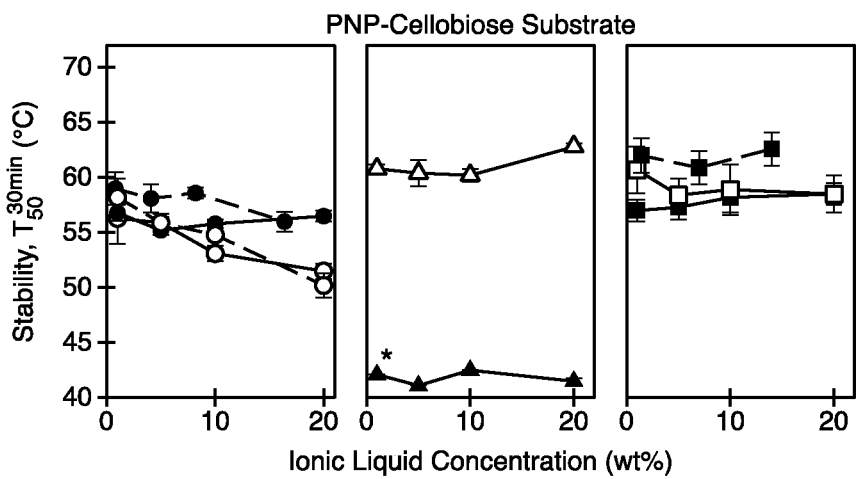
FIG. 1B shows the stability of Ctec2 in ionic liquids as a function of concentration, assessed using PNP-cellobiose as the enzyme substrate.
Figure 1C:
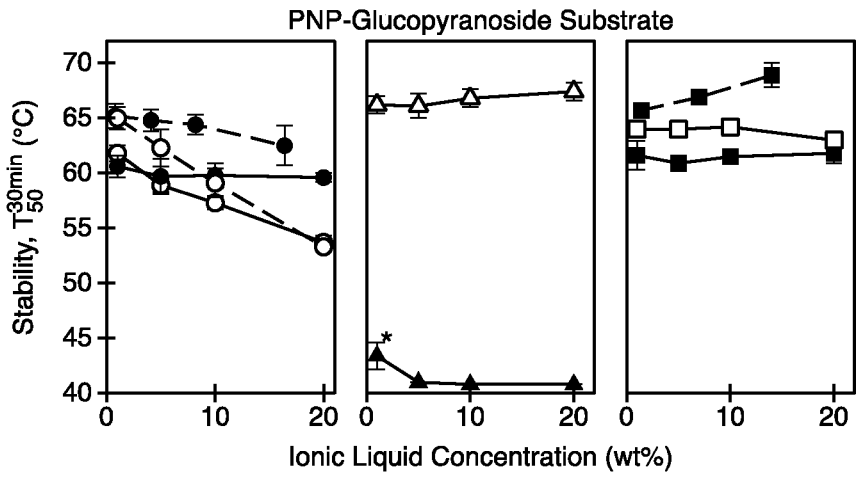
FIG. 1C shows the stability of Ctec2 in ionic liquids as a function of concentration, assessed using PNP-glucopyranoside as the enzyme substrate.

Data for CMC, PNP-cellobiose, and PNP-glucopyranoside is shown in FIGS. 1A, 1B, and 1C, respectively. In FIG. 1, data for acetate-based ionic liquids are shown in the left-hand panels: [Em][Ac] (open circle, solid line); [Ch][Ac] (closed circle, solid line); [Na][Ac], pH ~5.2 at 25° C. (closed circle, dashed line). Data for glutamic acid-based ionic liquids are shown in the center panels: [Ch][Glu] (open triangle, solid line); [Ch]$_2$[Glu] (closed triangle, solid line); [Em][Ac]:[H][Ac] 3:1, pH ~5.2 at 25° C. (open circle, dashed line). Data for succinic acid-based ionic liquids are shown in the right-hand panels: [Ch][Sc] (open square, solid line); [Na][Sc], pH ~5.2 at 25° C. (closed square, dashed line); [Ch]$_2$[Sc] (closed square, solid line). Error bars represent ±1 standard deviation of triplicate measurements. $T_{50}^{30}$ values below 45° C. are too low to report accurately but are included for completeness.

As shown in FIG. 1, the $T_{50}^{30}$ values around 60-65° C. are all in solutions with a pH of ~5, while the $T_{50}^{30}$ values around 50° C. are in pH 7 solutions. The [Ch]$_2$[Glu] curve with the lowest $T_{50}^{30}$ values measured has a pH ~10-11. CTec2 activity was very low even at the lowest [Ch]$_2$[Glu] concentrations. A similarly low $T_{50}^{30}$ was found for CTec2 in [Ch][Lys], which has a solution pH of ~14. The acidic form of the succinate and glutamate-based ILs was compared with [Em][Ac] (20%) acidified with acetic acid to a pH ~5. When the acidified [Em][Ac] was used, the stability of the commercial enzyme mixture decreased significantly on the para-nitrophenol substrates and slightly on CMC. The resulting values were lower than the same pH and concentration conditions with the choline succinate or glutamate ionic liquids.

The low $T_{50}^{30}$ values for [Ch]$_2$[Glu] suggested that enzyme instability was predominantly due the pH being far from the pH optimum of ~5 for CTec2; however, the results obtained using acidified [Em][Ac] show that reduced enzyme stability is due at least in part to factors other than pH incompatibility when [Em][Ac] is used in one-pot pretreatment and saccharification processes. The use of the di-carboxylic acid ionic liquids for the pretreatment biomass was investigated next, prompted by the stability of the commercial enzyme mixture in these ionic liquids.

Example 3. Biomass Pretreatment and Saccharification

Putnam Switchgrass (20 mesh—2 mm particle size) was used as the biomass for all experiments. Samples used to determine the pretreatment and dilution efficiency were washed free of ionic liquid with de-ionized water, and re-suspended in 50 mM sodium succinate buffer at pH 5.2. All enzyme hydrolysis reactions were performed with shaking at 50° C. and 20 mg/g 9:1 Ctec2:Htec, unless otherwise specified. Small-scale, one-pot reactions were performed in 2 ml screw-cap vials in heating blocks without mixing with 100 mg biomass at the specified ionic liquid concentration and biomass loading. Reactions were then acidified with 1 eq. of the free acid in the same vial and transferred to shaker incubators for the enzymatic hydrolysis. Larger scale one-pot reactions were performed in glass pressure tubes (Ace Glass, USA) with 2 g or 4 g biomass (Table 1). Liberated glucose and xylose were quantified with an Agilent HPLC using a Bio-Rad Aminex HPX-87P column with a 4 mM sulfuric acid mobile phase.

Figure 2A:
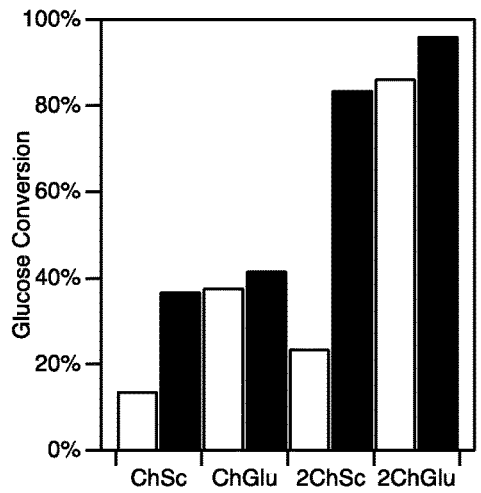
FIG. 2A shows sugar conversion levels resulting from pretreatment and enzymatic hydrolysis of switchgrass conducted according to the method of the invention.
Figure 2B:
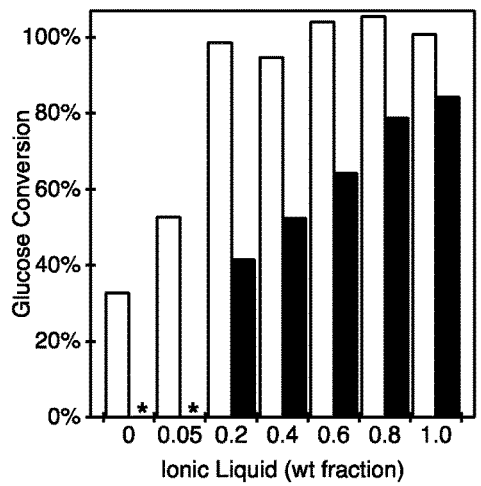
FIG. 2B shows dilution pretreatment efficiency for pretreatment and enzymatic hydrolysis of switchgrass conducted according to the method of the invention.

FIG. 2 shows the sugar yield from pretreated biomass. FIG. 2A shows sugar conversion after pretreatment in neat ionic liquids and enzymatic hydrolysis in 50 mM sodium succinate, pH 5.2 buffer. Data for pretreatment at 90° C. and 120° C. is shown using white bars and black bars, respectively. Each reaction was performed as described in the methods in duplicate with <5% difference observed between samples. FIG. 2B shows glucose yields following at 120° C. for 3 hrs with [Ch]$_2$[Sc] (black bars) and [Ch]$_2$[Glu] (white bars), and dilution of the ionic liquid to 25% with water.

TABLE 1

One-pot pretreatment/saccharification conditions.

| No. | Biomass Amount (g) | Biomass Loading (wt %) | Ionic Liquid Loading (wt %) | Temperature (° C.) | Pretreatment/ Saccharification Times (hrs) | Replicates, Experiments |
| --- | --- | --- | --- | --- | --- | --- |
| 1 | 2.0 | 10 | 10 | 120 | 6/72 | 2, PS |
| 2 | 2.0 | 25 | 25 | 120 | 3/72 | 2, PS |
| 3 | 2.0 | 25 | 25 | 150 | 3/72 | 2, PS |
| 4 | 4.0 | 10 | 10 | 120 | 6/120 | 1, PSF |
| 5 | 4.0 | 10 | 25 | 120 | 3/120 | 1, PSF |

DCA-ILs were found to pretreat biomass poorly when only one of the acid groups was deprotonated, as demonstrated by the results obtained using [Ch][Sc] (pH ~4-6) and [Ch][Glu] (pH ~5-7) shown in FIG. 2A. Another study with amino-acid based ionic liquids resulted in a similar finding [Liu, et al. 2012. *Green Chemistry* 14: 304-7]. However, the pretreatment shows a marked improvement when both acid groups are deprotonated, as demonstrated by the results obtained using [Ch]$_2$[Sc] and [Ch]$_2$[Glu] shown in FIG. 2A. The effectiveness of the pretreatment does not appear to depend on pH alone, however, as shown in the different results obtained for [Ch]$_2$[Sc] and [Ch][Glu]. [Ch]$_2$[Sc] and [Ch][Glu] have similar solution pHs near 7, but [Ch]$_2$[Sc] pretreatment at 120° C. allows for the release of twice as much sugar.

Without wishing to be bound by any particular theory, it is believed that ionic liquids with high basicity effectively extract lignin (an important parameter for ionic liquids that do not completely dissolve biomass). This is supported by the observation that [Ch]$_2$[oxalic acid], with completely deprotonated but much more acidic carboxylic acid groups, only gives a glucose conversion of 48% when used neat, only ~15% higher than hot water pretreatment and about as well as 5% [Ch]$_2$[Glu].

Dilution of ILs has been reported as one method to reduce ionic liquid cost as long as the ionic liquid remains effective. Other ionic liquids have been shown to work in dilute solution [Hou, et al. 2013. *Bioresource Technology* 136:

469-74; Hou, et al. 2013. *Biotechnology and Bioengineering* 110: 1895-1902]. [Ch][Glu] demonstrated similar effects. FIG. 2B shows dilutions of [Ch]$_2$[Sc] and [Ch]$_2$[Glu] give qualitatively different profiles for pretreatment efficiency. Choline glutamate shows a consistently high pretreatment efficiency even after dilution to ~20 wt %, while choline succinate shows a monotonic decrease in efficiency as it is diluted.

Figure 2C:
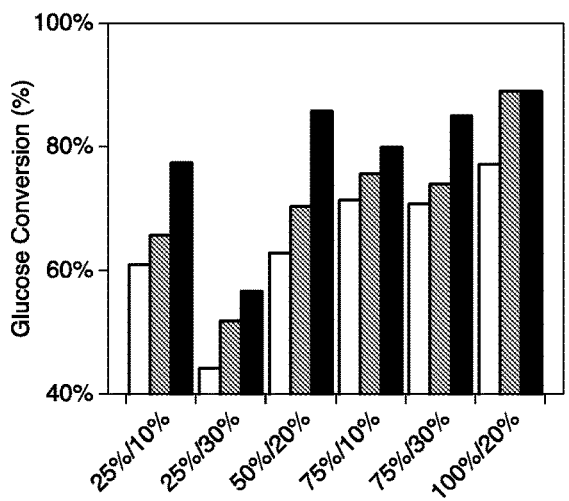
FIG. 2C shows glucose conversion levels for one-pot pretreatment and enzymatic hydrolysis conducted under various conditions.

Pretreatment and enzymatic hydrolysis of switchgrass in the presence of choline glutamate is shown in FIG. 2C, which demonstrates the combined effects of [Ch]$_2$[Glu] concentration and biomass loading on glucose yields. For the data in FIG. 2C, samples were pretreated at 90° C. or 120° C., with various % IL in the liquid fraction and different wt % biomass loadings. All samples were then hydrolyzed at 25% IL concentration with 9:1 Ctec2:Htec at 20 mg/g biomass. White bars, 90° C., 16 hrs; gray bars, 120° C., 3 hrs; black bars, 120° C., 16 hrs.

Pretreatment and saccharification were performed at various (%[Ch]$_2$[Glu]/biomass loadings) ratios under three pretreatment temperature and time conditions, pH was adjusted by addition of one equivalent of [Glu] and saccharification reactions were run following dilution of the resulting solution to 25% [Ch][Glu]. Across the five scenarios presented, pretreatment at 120° C. for 16 hours resulted in higher glucose yields, but pretreatment time became less of a factor as the concentration of [Ch]$_2$[Glu] increased. However, the longer pretreatment time at the higher temperature allowed for large reductions in the amount of [Ch]$_2$[Glu] required as the (50% [Ch]$_2$[Glu]/20% biomass loading) case resulted in a nearly identical glucose yield to the (100% [Ch]$_2$[Glu]/20% biomass loading) case and the 25% solution of [Ch]$_2$[Glu] performs ~90% as well as the neat ionic liquid.

Figure 3A:
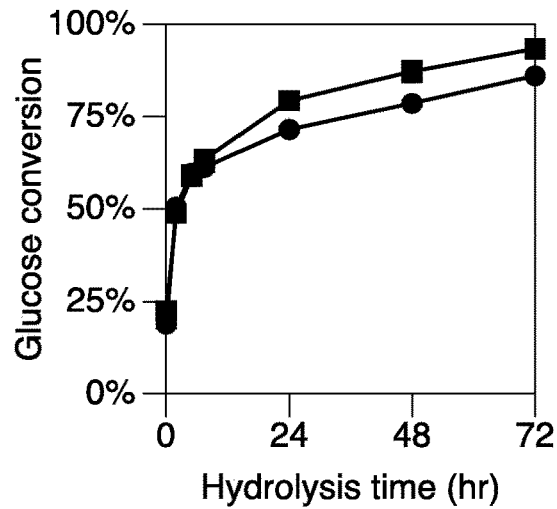
FIG. 3A shows glucose conversion levels for larger scale one-pot pretreatment and saccharification reactions.
Figure 3B:
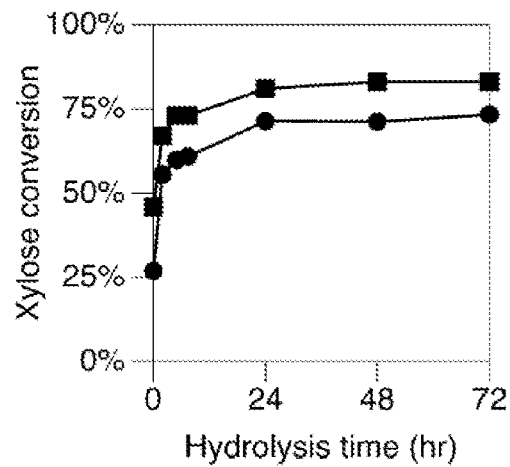
FIG. 3B shows xylose conversion levels for larger scale one-pot pretreatment and saccharification reactions.
Figure 3C:
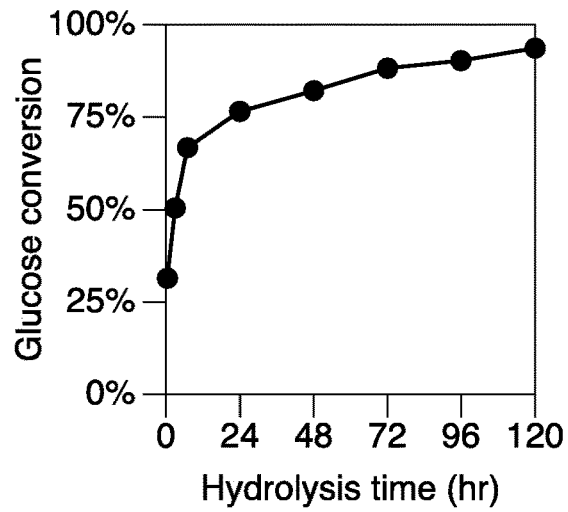
FIG. 3C shows glucose conversion levels for larger scale one-pot pretreatment and saccharification reactions.
Figure 4:
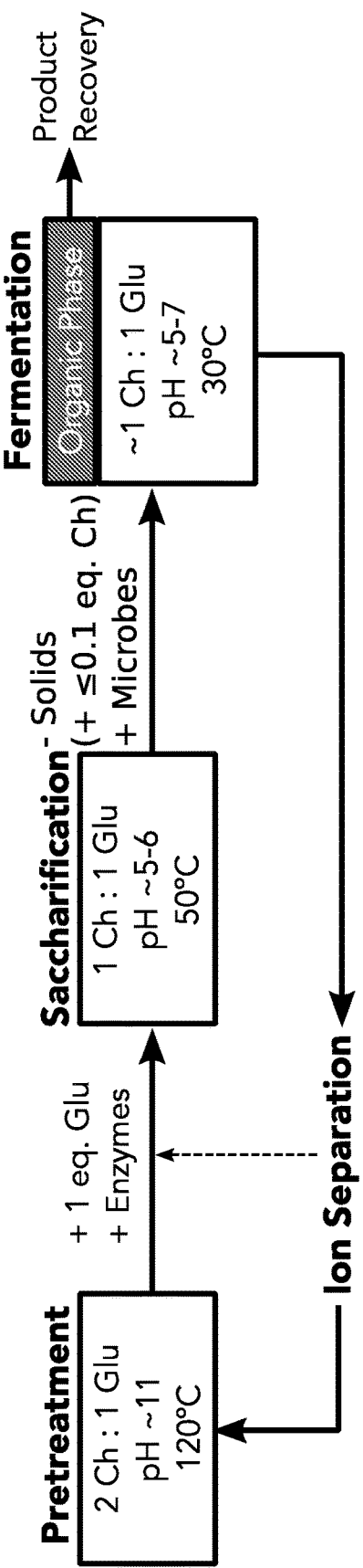
FIG. 4 shows one-pot switchable IL processes according to the methods of the invention.

Based on the small-scale screening of pretreatment and hydrolysis, larger reactions were performed in stirred pressure tubes at the lower concentrations tested. Results are shown in FIG. 3. FIG. 3A and FIG. 3B show the time course of enzymatic hydrolysis of 10% switchgrass in 10 wt % [Ch][Glu] or 25 wt % [Ch][Glu] using the CTec2. The hydrolysis was conducted following: 1) pretreatment of the switchgrass at 120° C. with [Ch]$_2$[Glu] at the same concentration, and 2) addition of one equivalent of glutamic acid to reduce the pH to levels close to the pH optimum of CTec2 (pH ~5.5). In FIG. 3A and FIG. 3B, the circles represent data obtained using 10 wt % ionic liquid and the squares represent data obtained using 25 wt % ionic liquid.

Glucose conversion reached 91% for 10 wt % [Ch][Glu] samples, and 82% [Ch][Glu] for 25 wt % samples. Over the course of hydrolysis, glucose concentration continued to increase after 24 hours (FIG. 3A), while the xylose conversion leveled off after the first 24 hours (FIG. 3B). Pretreatment of corn stover at 25 wt % [Ch]$_2$[Glu] yielded similarly high glucose (~95%) yields. Improved pretreatment was observed with longer incubation times or mixing, indicating a kinetic or mass transfer limitation to the pretreatment step.

Example 4. Microbial Growth and Fermentation

To date, ionic liquids shown to efficiently pretreat biomass and produce high fermentable sugar yields have also been reported to be harmful to fermentation hosts even at very low concentrations, requiring either extensive and costly washing steps to remove residual IL or engineering the host to tolerate the IL. While both approaches have been successful, extensive washing is cost prohibitive and engineering *E. coli* for tolerance has resulted in engineered strains capable of growth in only 2 to 3% [C$_2$C$_1$Im][Cl], which only slightly reduces the requirements for extensive washing. Tolerance of ionic liquids by fermentative hosts is thus a limiting condition for the amount of residual ionic liquid remaining during fermentation.

*E. coli* DH10B was screened for growth in 96-well clear-bottom plates in a plate reader (Tecan, Infinite 200) at 37° C. Seed cultures were grown overnight in LB media, and then diluted to $OD_{600\ nm}$ of 0.01 in EZ-Rich defined media (Teknova, USA) containing 0-30% choline glutamate or choline succinate. Growth was monitored for up to 40 hours and specific growth rate were calculated from the initial exponential growth phase. Hydrolysate for fermentation experiments was generated from pretreatment and saccharification reactions with 4 g biomass at 10 or 25 wt % choline glutamate. The final hydrolysate was centrifuged to remove residual solids, pH adjusted with the basic form of the ionic liquid (2:1 stoichiometry), and then the liquid fraction was then used to prepare the growth media.

Figure 5A:
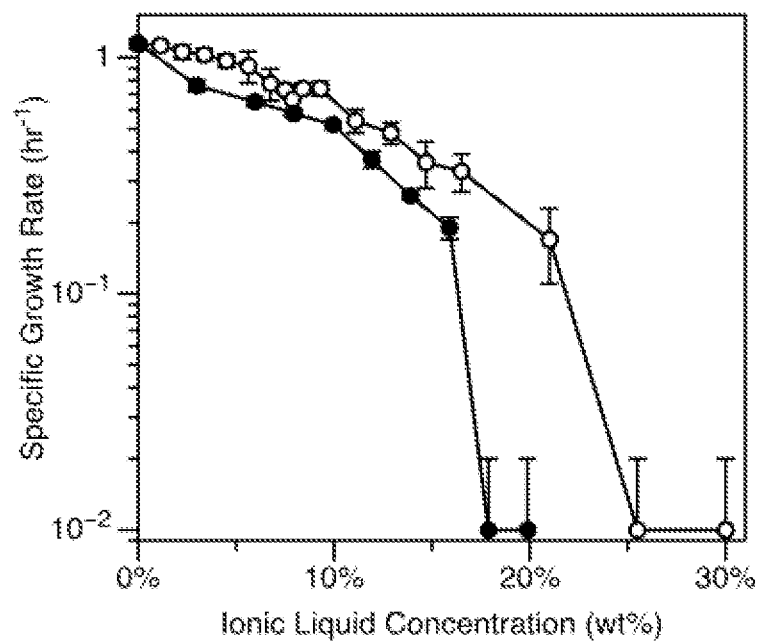
FIG. 5A shows the growth rate of *E. coli* on switchgrass hydrolysates in [Ch][Glu] and [Ch][Sc].

Growth of *S. cerevisiae* was measured in [Ch][Sc], [Ch]$_2$[Sc], and [Ch][Glu] in concentrations up to 20%. Growth of *E. coli* was measured in [Ch][Sc], [Ch]$_2$[Sc], and [Ch][Glu] in concentrations up to 25%. FIG. 5A the shows growth rate of *E. coli* on switchgrass hydrolysates in [Ch][Glu] (open circles) and [Ch][Sc] (solid circles).

The pH of either the neat ionic liquid or hydrolysate was found to have the largest effect on the growth of both *E. coli* and *S. cerevisiae*. In the presence of [Ch][Sc] at a pH of ~5, *E. coli* growth was inhibited at concentrations above 3%, while *S. cerevisiae* maintained its maximum growth rate up to 10% IL. In [Ch]$_2$[Sc], at a pH ~7, *E coli* could grow up to ~15 wt %. In [Ch][Glu] growth was observed up to 20%, with the cultures reaching the same maximum OD up to 15%. The growth in these ILs continues to orders of magnitude higher concentrations where other ILs inhibit growth [Ouellet, et al. 2011. *Green Chemistry* 13: 2743-49].

The hydrolysates were tested for common inhibitors produced during pretreatment. As the ionic liquid concentration increased, the amount of dissolved lignin fragments increased. Table 2 shows some of the common inhibitors identified in the hydrolysate; no furfural or 5-hydroxymethylfurfural (HMF) were identified. Without wishing to be bound by any particular theory, it is believed that the surprisingly robust growth of microorganisms during fermentation may result from the lack of inhibitors such as furfural and HMF in the hydrolysates. The limited production of inhibitors may be due to the narrower pH range of the choline glutamate process, versus more extreme alkaline and/or acidic conditions employed in other processes.

TABLE 2

Compounds in hydrolysate identified by LC/MS

| Compound | Formula | RT | m/z | 10% IL | 25% IL |
|---|---|---|---|---|---|
| Furfural | $C_5H_4O_2$ | * | 95.01 | * | * |
| 5-Hydroxymethyl-furfural | $C_6H_6O_3$ | * | 125.02 | * | * |
| 4-Hydroxybenz-aldehyde | $C_7H_6O_2$ | 5.16 | 121.03 | 942,826 | 766,190 |
| 4-Hydroxybenz-aldehyde | $C_7H_6O_2$ | 5.95 | 121.03 | 122,123 | 157,616 |
| Syringaldehyde | $C_9H_{10}O_4$ | * | 181.05 | * | * |
| Vanillin | $C_8H_8O_3$ | 5.60 | 151.04 | 18,617 | 13,920 |
| Vanillic Acid | $C_8H_8O_4$ | 4.15 | 167.03 | 27,752 | 36,779 |
| Levulinic Acid | $C_5H_8O_3$ | 3.26 | 115.04 | 28,560 | 30,293 |
| 4-Hydroxybenzoic Acid | $C_7H_6O_3$ | 4.00 | 137.02 | 177,116 | 126,293 |

TABLE 2-continued

Compounds in hydrolysate identified by LC/MS

| | | | | Peak Area | |
|---|---|---|---|---|---|
| Compound | Formula | RT | m/z | 10% IL | 25% IL |
| p-Coumaric Acid | $C_9H_8O_3$ | 4.84 | 163.04 | 1,091,498 | 2,805,354 |
| Syringic Acid | $C_9H_{10}O_5$ | 4.10 | 197.05 | 14,159 | 16,406 |
| Coumaryl alcohol | $C_9H_{10}O_2$ | 5.52 | 151.08 | 117,574 | 179,352 |
| Coumaryl alcohol | $C_9H_{10}O_2$ | 5.76 | 151.08 | 82,926 | 131,938 |
| Coumaryl alcohol | $C_9H_{10}O_2$ | 7.36 | 151.08 | 164,145 | 92,767 |
| Hydroquinone | $C_6H_6O_2$ | 6.39 | 111.04 | 23,600 | 44,377 |

\* indicates that the compounds were not observed by LC/MS.

Example 5. Isopentenol Production from Fermentation Host (*E. coli*) in DCA-IL

With growth in the neat ionic liquids established, the production of isopentenol (3-methyl-3-buten-1-ol), an advanced biofuel with promising fuel properties, in hydrolysates was used to monitor fermentation efficiency in the presence of [Ch][Sc] and [Ch][Glu]. Isopentenol was prepared via fermentation of hydrolysates using *E. coli* BW25113 harboring two plasmids: pBbA5c-MevTsa-MK-PMK for expression of melavonate kinase and pTrc99a-rNudB-PMD for expression of *E coli* phosphatase NudB. See, George, et al. (*Biotechnol Bioeng* 111, 1648-1658 [2014]). Seed cultures were prepared by growing a single colony overnight in LB media containing 100 μg/ml ampicillin and 30 μg/ml chloramphenicol at 37° C. The overnight seed cultures were diluted to an $OD_{600\ nm}$ of 0.07 in 4 ml EZ-Rich media containing 10.8 g/L glucose, 6.4 g/L xylose, 100 μg/ml ampicillin and 30 μg/ml chloramphenicol with different treatments. Four treatments were 10% choline glutamate, 25% choline glutamate and two different hydrolysate solutions obtained from 10%-choline glutamate treated biomass and 25%-choline glutamate treated biomass, respectively. Each of these four treatments was added to the EZ-Rich media at volumes of 0, 10, 25, or 50% (v/v). All cultures were grown at 37° C. until the $OD_{600\ nm}$ reached 0.6-0.8, at which point isopentenol fermentation was initiated by addition of 0.5 mM IPTG. The fermentation was continued at 30° C. for 90 hours. Aliquots of 150-300 μL were collected for determination of $OD_{600\ nm}$, quantification of sugars, and quantification of isopentenol.

For isopentenol analysis, equal parts cell culture and ethyl acetate (containing 30 mg/L 1-butanol as an internal standard) were mixed for 15 minutes then centrifuged to separate the ethyl acetate phase from aqueous phase. The ethyl acetate phase was diluted 5-fold and 1 μL was analyzed with an Agilent GCMS equipped with Cyclosil-B column.

Figure 5B:
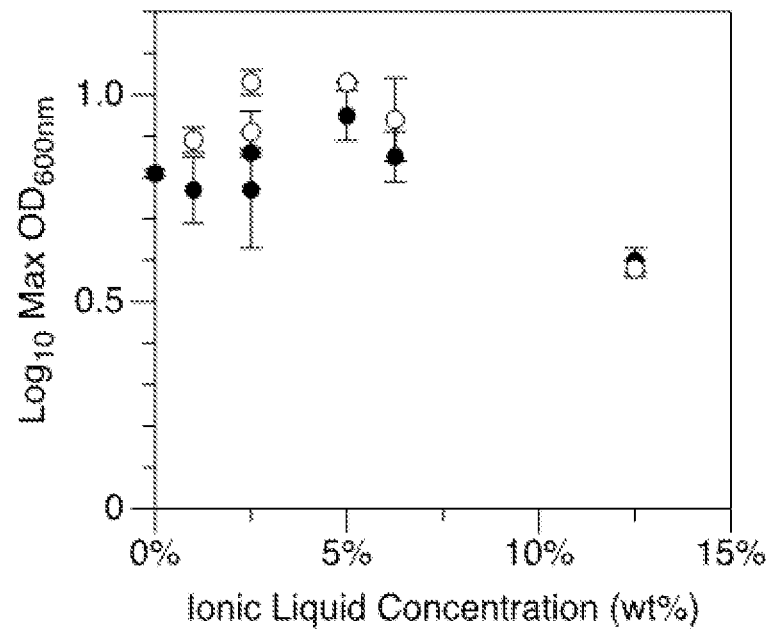
FIG. 5B shows the max $OD_{600\ nm}$ obtained during isopentenol production using glucose and xylose in EZ-dex media+[Ch][Glu], or using hydrolysates obtained according to the methods of the invention+[Ch][Glu].
Figure 6:
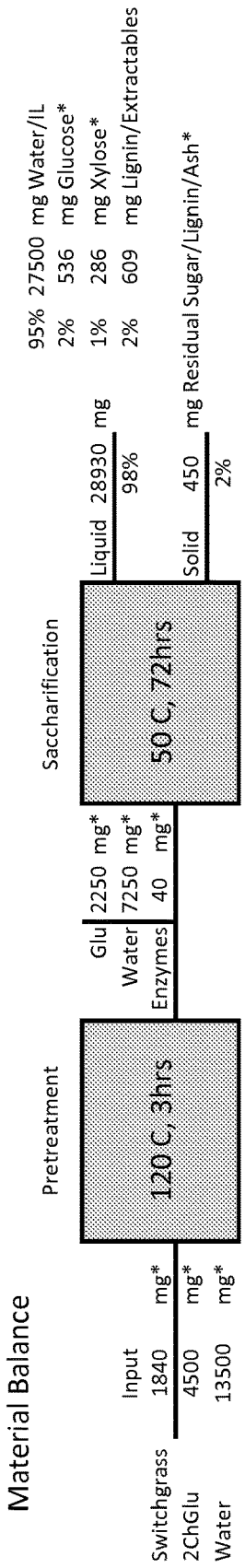
FIG. 6 shows a schematic representation of a process including pretreatment and saccharification of switchgrass using the method of the invention.

For isopentenol production from 50% (v/v) of hydrolysate produced from enzymatic hydrolysis and pretreatment in the presence of 25% [Ch][Glu], the *E. coli* host was serially adapted to EZ-Rich media containing 25% and 50% (v/v) of hydrolysate with 25% [Ch][Glu]. First, overnight culture (LB) of the host strain was diluted to EZ-Rich media containing 25% (v/v) of the hydrolysates with 25% [Ch][Glu] and grown at 37° C. When the cell cultures reached at $OD_{600\ nm}$ of 3.6-4 they were diluted 10 times in a fresh EZ-Rich media supplemented with 50% (v/v) of the same hydrolysates and grown overnight (14 hours). On the following day, the overnight cultures ($OD_{600\ nm}$ of 3.7-4.4) were diluted 20 times in fresh EZ-Rich media supplemented again with 50% (v/v) hydrolysates with 25% [Ch][Glu] for isopentenol production. As positive controls, the adapted production strains were also diluted in EZ-Rich media without hydrolysates. All six tubes were incubated at 37° C. until $OD_{600\ nm}$ reached 0.6-0.8, and the isopentenol fermentation was conducted as described above. FIG. 5B shows the max OD observed during isopentenol production on glucose and xylose in EZ-dex media+[Ch][Glu] (open circles) and on hydrolysates+[Ch][Glu] (solid circles).

Isopentenol yields on switchgrass hydrolysates using *E. coli* strains metabolically engineered to produce isopentenol from acetyl-CoA via the heterologous mevalonate pathway are shown in Table 3.

TABLE 3

Isopentenol Yield after 48 hrs from *E. coli* in dilutions in EZ-dex media with 10 and 25% [Ch][Glu] and added glucose and xylose or from hydrolysate solutions\*

| | Isopentenol Yield (mg/L) | | |
|---|---|---|---|
| Dilution factor | 10-Fold | 4-Fold | 2-Fold |
| 10% [Ch][Glu] + Sugars | 1178 ± 63 | 1087 ± 48 | 928 ± 34 |
| 10% [Ch][Glu] Hydrolysate | 1199 ± 128 | 1058 ± 133 | 661 ± 24 |
| 25% [Ch][Glu] + Sugars | 1182 ± 66 | 816 ± 39 | 492 ± 38 |
| 25% [Ch][Glu] Hydrolysate | 1228 ± 155 | 938 ± 56 | 275 ± 32 |
| Control Media + Sugars | | 973 ± 106 | |

\*Hydrolysates generated from either 10% or 25% [Ch][Glu] solutions were diluted for use as the carbon source in growth and fermentation experiments. Control experiments were performed with neat ionic liquids plus sugars and only EZ-dex growth media. See methods section for details of fermentation experiments.

Figure 8A:
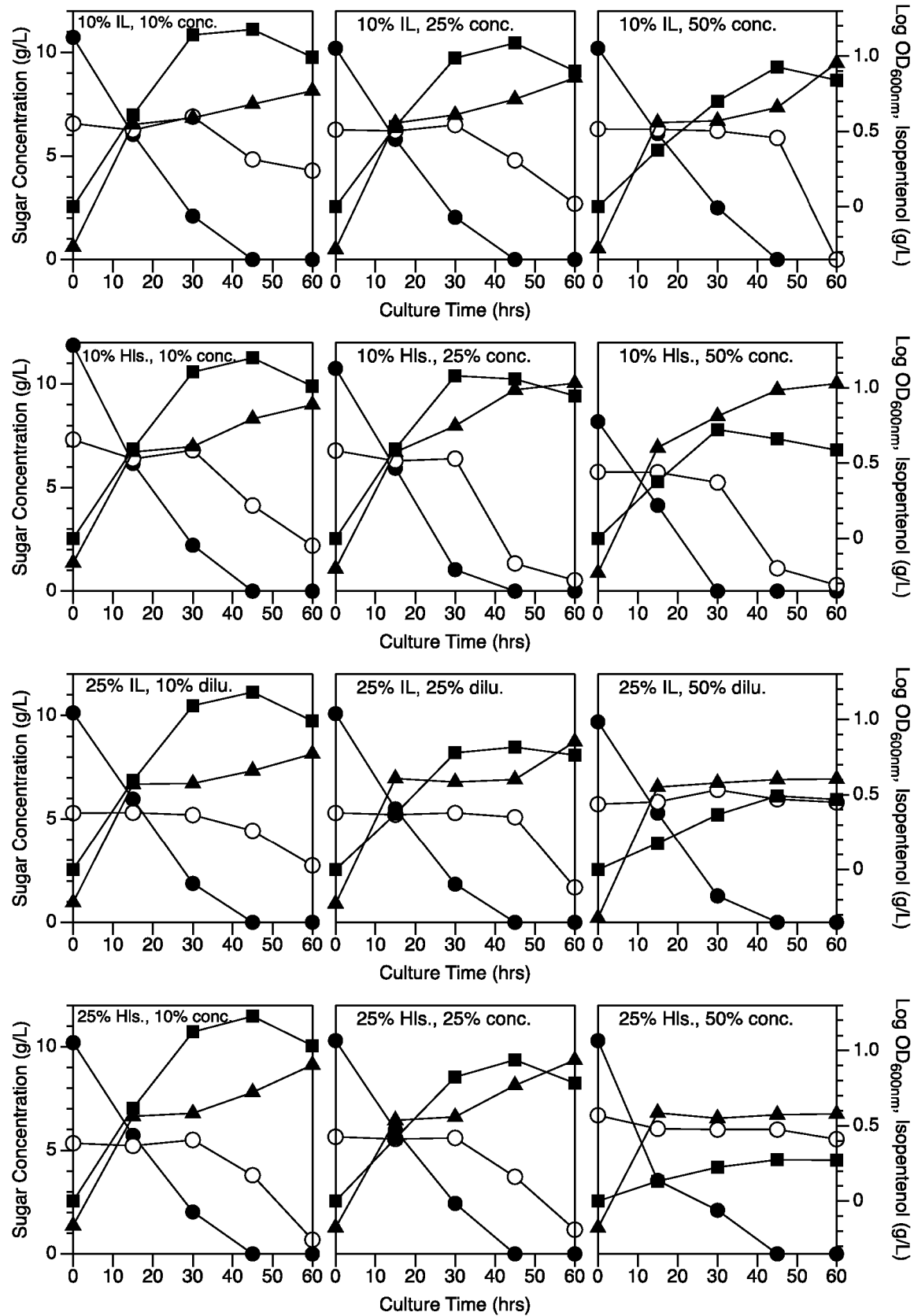
FIG. 8A shows growth of *E. coli*, sugar consumption by *E. coli*, and isopentenol production by *E. coli* plotted over time during isopentenol production using hydrolysate sugar compositions prepared according to the methods of the invention.
Figure 8B:
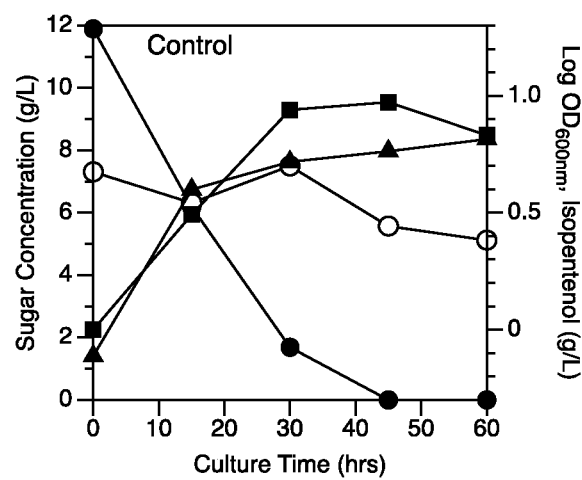
FIG. 8B shows growth of *E. coli*, sugar consumption by *E. coli*, and isopentenol production by *E. coli* plotted over time during isopentenol production using a control culture containing added glucose and xylose.

Two pretreatment and saccharification conditions, 10% and 25% [Ch][Glu], were tested to identify fermentation-modulating differences in hydrolysates produced from different ionic liquid concentrations. The production of isopentenol remained near the level of the no-IL control for all of the 4-fold diluted samples, and at a 2-fold dilution for the 10% neat [Ch][Glu]+sugar sample. Significant reduction of isopentenol yields did not occur until fermentation was conducted in media containing ~12% [Ch][Glu]. As shown in Table 2, higher concentrations of the IL during pretreatment liberated several phenolic compounds in the biomass hydrolysate, which can have inhibitory effects on bacterial growth. See, Jönsson, et al. *Biotechnol Biofuels* 6, 1-1 (2013). On the other hand, improved yields in the presence of moderate concentrations of IL and hydrolysates could be due to glutamate-induced stress responses, which might improve fitness of the *E. coli* in the presence of IL and other toxic hydrolysates. See, Foster, J. W. *Nat Rev Micro* 2, 898-907 (2004). Upon complete consumption of glucose, the host strain grown in moderate percentage of hydrolysates also had a faster xylose consumption rate than that in the absence of IL or hydrolysates (FIG. 8). FIG. 8 shows time-course plots for growth, sugar consumption, and isopentenol production: glucose concentration (g/L), closed circles; xylose concentration (g/L), open circle; $log_{10}$ culture OD, triangles; isopentenol concentration (g/L), squares. This suggests there are unknown mechanisms, possibly induced by phenolic compounds in the hydrolysates, that increase the xylose uptake rate. Interestingly, this xylose consumption did not lead to an increased isopentenol titer.

Contemporary ionic liquid synthesis has largely overlooked di-carboxylic acid anions for use in biomass pretreatment due to the low solubility of lignin and cellulose in the singly-deprotonated form [Ninomiya, et al. 2013 *Biochemical Engineering Journal* 71: 25-29; Liu et al. 2012, supra; Boissou, et al. 2014. *Green Chemistry* 16: 2463-71]. Even one-pot processes based on [Em][Ac] are limited by reduced enzyme stability and a high ionic liquid cost. See, e.g., FIG. 1 and Shi, et al. 2013 supra.

Removal of a single choline cation to switch the pH has the advantage of reducing water use for washing away the ionic liquid. Choline lysinate ([Ch][Lys]) has a solution pH of ~12 and requires tens of volumes of water to sufficiently dilute the ionic liquid. Even in dilute solution, [Ch][Lys] produces too basic a solution for any known cellulase, therefore buffer is required to adjust the final pH. With DCA-ILs the singly-protonated form of the anion determines the pH of the solution, thus buffer is not needed to set the final pH. Since the final IL solution has the correct pH, the required dilution is determined by the stability and activity of the enzyme cocktail in the IL. Since the same set of ions is used throughout the process, there is no need to remove ions used to adjust the pH before recycling.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A method for preparing a sugar composition, the method comprising:
   i) forming a mixture comprising polysaccharide biomass and an ionic liquid solution, wherein
      the ionic liquid solution comprises water and an ionic liquid,
      the ionic liquid comprises a dicarboxylic acid anion and a choline cation,
      the pH of the mixture is greater than or equal to about 10, and
      the molar ratio of the dicarboxylic acid anion to the cation is at least about 1:2;
   ii) maintaining the mixture at the pH greater than or equal to about 10 under conditions sufficient to dissolve at least a portion of the polysaccharide present in the polysaccharide biomass;
   iii) reducing the pH of the mixture containing the ionic liquid and the dissolved polysaccharide to at least about 7 by adding the same dicarboxylic acid used in step i) to the mixture,
      wherein the amount of the added dicarboxylic acid is equal to the molar amount of the dicarboxylic acid in step i), so that the molar ratio of the dicarboxylic acid anion to the cation is about 1:1;
   iv) adding at least one glycoside hydrolase to the mixture containing the ionic liquid and the dissolved polysaccharide and having the reduced pH; and
   v) maintaining the mixture containing the ionic liquid, the dissolved polysaccharide, and the glycoside hydrolase and having the reduced pH under conditions sufficient to hydrolyze at least a portion of the dissolved polysaccharide, thereby forming the sugar composition;
   wherein the sugar composition comprises at least one monosaccharide or oligosaccharide.

2. The method of claim 1, wherein the dicarboxylic acid is selected from the group consisting of a $C_{3-16}$ alkane-dioic acid and a $C_{3-16}$ alkene-dioic acid; wherein the dicarboxylic acid is branched or unbranched; and wherein the dicarboxylic acid is optionally substituted with from one to three substituents selected from the group consisting of amino, hydroxy, and oxo.

3. The method of claim 2, wherein the dicarboxylic acid is selected from the group consisting of adipic acid, aspartic acid, azelaic acid, dodecanedioic acid, fumaric acid, glutamic acid, glutaric acid, maleic acid, malonic acid, pimelic acid, sebacic acid, suberic acid, succinic acid, undecanedioic acid, and mixtures thereof.

4. The method of claim 1, wherein the ionic liquid solution comprises from about 70% (w/w) to about 95% (w/w) water.

5. The method of claim 1, wherein the ionic liquid solution comprises 75-90% (w/w) water; and further comprises 10-25% dicholine glutamate (w/w) or 10-25% dicholine succinate (w/w).

6. The method of claim 1, wherein the mixture in step i) comprises from about 5% (w/w) to about 30% (w/w) polysaccharide biomass.

7. The method of claim 1, wherein step ii) comprises maintaining the mixture of step i) at a temperature of at least about 100° C. for at least about 30 minutes.

8. The method of claim 1, wherein the polysaccharide biomass comprises cellulose, hemicellulose, lignocellulose, or mixtures thereof.

9. The method of claim 1, wherein the glycoside hydrolase is a cellulase.

10. The method of claim 1, wherein the glycoside hydrolase is selected from the group consisting of an endoglucanase, an exoglucanase, a β-glucosidase, a xylanase, and mixtures thereof.

11. The method of claim 1, comprising:
   i) forming a mixture comprising switchgrass and an ionic liquid solution,
      wherein the ionic liquid solution comprises about 10-25% (w/w) dicholine glutamate and about 75-90% (w/w) water, and
      wherein the pH of the mixture is at least about 11;
   ii) maintaining the mixture containing the switchgrass and the dicholine glutamate at about 120° C. for about three hours, thereby dissolving the lignocellulose present in the switchgrass;
   iii) adding glutamic acid to the mixture containing the dicholine glutamate and the dissolved lignocellulose, wherein the amount of glutamic acid is equal to the amount of glutamate in step i);
   iv) adding at least one glycoside hydrolase to the mixture containing the glutamic acid, the dicholine glutamate, and the dissolved lignocellulose resulting from step iii); and
   v) maintaining the mixture containing the glutamic acid, the dicholine glutamate, the dissolved lignocellulose, and the glycoside hydrolase at about 50° C. for about 72 hours, thereby forming the sugar composition;
   wherein the sugar composition comprises glucose.

12. A method for converting a sugar composition to a fermentation product, the method comprising fermenting a mixture containing a sugar composition prepared according to the method of claim 1.

13. The method of claim 12, wherein the fermenting is conducted without removing the ionic liquid from the mixture containing the sugar composition.

14. The method of claim 13, wherein the fermenting comprises adding a fermentation microorganism to the mixture containing the sugar composition and the ionic liquid.

15. The method of claim 12, wherein the fermentation product is isopentenol or a bisabolene.

16. The method of claim 1, wherein the dicarboxylic acid is selected from the group consisting of glutamic acid and succinic acid.

17. The method of claim 1, wherein the dicarboxylic acid is glutamic acid.

\* \* \* \* \*